United States Patent
Toleikis et al.

(10) Patent No.: US 8,969,318 B2
(45) Date of Patent: Mar. 3, 2015

(54) BISPECIFIC APTAMERS MEDIATING TUMOUR CELL LYSIS

(75) Inventors: Lars Toleikis, Kleinniedesheim (DE); Ralf Guenther, Griesheim (DE); Bjoern Hock, Maintal (DE); Achim Doerner, Marburg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/992,608

(22) PCT Filed: Dec. 12, 2011

(86) PCT No.: PCT/EP2011/006254
§ 371 (c)(1), (2), (4) Date: Jun. 7, 2013

(87) PCT Pub. No.: WO2012/076190
PCT Pub. Date: Jun. 14, 2012

(65) Prior Publication Data
US 2014/0039042 A1    Feb. 6, 2014

(30) Foreign Application Priority Data
Dec. 10, 2010   (EP) ..................... 10015522

(51) Int. Cl.
A61K 48/00   (2006.01)
C07H 21/02   (2006.01)
C07H 21/04   (2006.01)
C12Q 1/68    (2006.01)

(52) U.S. Cl.
USPC ........................ 514/44 A; 536/24.5

(58) Field of Classification Search
USPC ........................... 536/24.5; 514/44
See application file for complete search history.

(56) References Cited

U.S. PATENT DOCUMENTS
2009/0215874 A1   8/2009   Sullenger et al.

FOREIGN PATENT DOCUMENTS
WO   WO-2007 035518   3/2007

OTHER PUBLICATIONS

Boltz, A. et al., "Bi-specific aptamers mediating tumor cell lysis," Journal of Biological chemistry, Jun. 17, 2011, vol. 286, No. 24, pp. 21896-21905.
Huang, Y-F. et al., "Cancer cell targeting using multiple aptamers conjugated on nanorods," Anal. Chem., 2008, vol. 80, pp. 567-572.
International Search Report for PCT/EP2011/006254, Date of the actual completion of the international search: Apr. 16, 2012, Date of mailing of the international search report: Apr. 26, 2012.
Mallikaratchy, P. R. et al., "A multivalent DNA aptamer specific for the B-cell receptor on human lymphoma and leukemia," Nucleic Acids Research, 2011, vol. 39, No. 6, pp. 2458-2469.
McNamara, J. O. et al., "Multivalent 4-1BB binding aptamers costimulate CD8+ T cells and inhibit tumor growth in mice," The Journal of Clinical Investigation, Jan. 2008, vol. 118, No. 1, pp. 376-386.
Pastor, F. et al., "Targeting 4-1BB Costimulation to Disseminated Tumor Lesions with Bi-Specific Oligonucleoptide aptamers," Molecular Therapy, Oct. 2011, vol. 19, No. 10.
Shahied, L. S. et al., "Bispecific minibodies targeting HER2/neu and CD 16 Exhibits Improved Tumor Lysis When Placed in a Divalent Tumor Antigen Binding Format," The Journal of Biological Chemistry, Dec. 24, 2004 vol. 279 No. 12 pp. 53907-53914.

*Primary Examiner* — Terra Cotta Gibbs
(74) *Attorney, Agent, or Firm* — Millen, White, Zelano, Branigan, P.C.

(57) ABSTRACT

Disclosed are bispecific aptamers binding with high specifity to a tumour specific antigen (TSA) and a effector cell specific antigen (ESA) for treatment of cancer.

8 Claims, 6 Drawing Sheets

Figure 1:
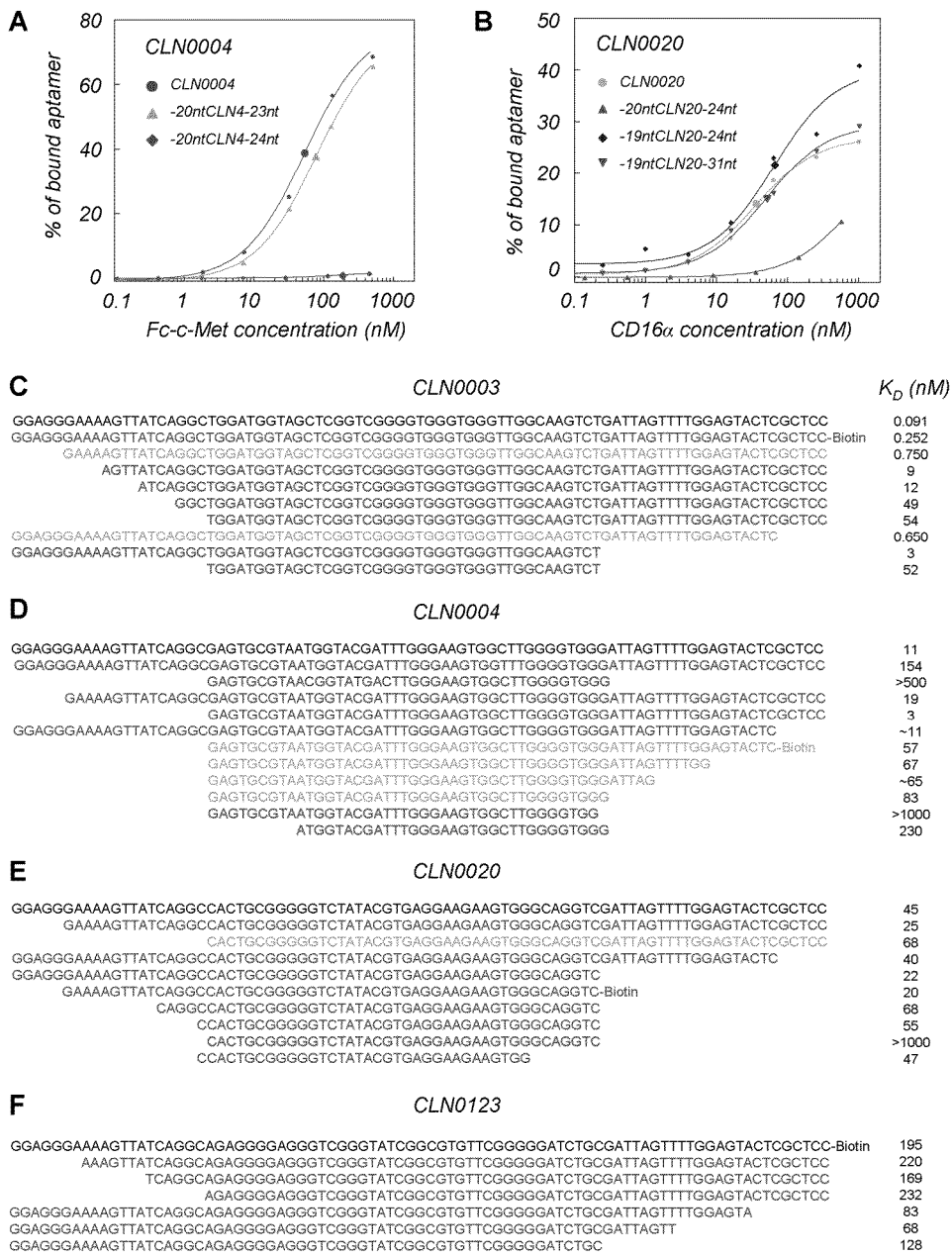

| Construct | CD16α-6His Kd (nM) | n | Fc-c-Met Kd (nM) | n |
|---|---|---|---|---|
| bsA1 | 84 | 1 | 319 | 1 |
| bsA2 | 51 | 1 | 220 | 1 |
| bsA3 | 39 ± 10 | 3 | 141 ± 16 | 6 |
| bsA31 | 24 ± 4 | 4 | 92 ± 41 | 3 |
| bsA32 | 33 ± 1 | 2 | 119 ± 22 | 3 |
| bsA4 | 78 | 1 | 105 | 1 |
| bsA5 | 64 | 1 | 164 | 1 |
| bsA6 | 51 | 1 | 370 | 1 |
| bsA7 | 73 | 1 | 160 | 1 |
| bsA8 | 102 | 1 | 271 | 1 |
| bsA9 | 98 ± 6 | 2 | 0.160 | 1 |
| bsA10 | 112 ± 5 | 2 | 0.157 | 1 |
| bsA11 | 82 ± 9 | 2 | 0.162 | 1 |
| bsA12 | 106 ± 17 | 2 | 18 | 1 |
| bsA13 | 197 ± 3 | 2 | 18 | 1 |
| bsA15 | 174 | 1 | 0.218 | 1 |
| bsA16 | 178 | 1 | 102 | 1 |
| bsA17 | 19 ± 2 | 3 | 0.352 ± 0.090 | 6 |
| bsA18 | 15 ± 2 | 2 | 106 ± 7 | 2 |
| bsA19 | 32 ± 0 | 2 | 38 ± 17 | 2 |
| bsA20 | 23 ± 4 | 2 | 5.2 ± 1.8 | 2 |
| bsA21 | 19 ± 2 | 2 | 0.276 ± 0.116 | 3 |
| bsA22 | 27 ± 5 | 2 | 0.243 ± 0.103 | 3 |

SEQUENCE LISTING

<160> NUMBER OF SEQ ID NOS: 137

<210> SEQ ID NO 1
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggagggaaaa gttatcaggc ggcagaagaa atatcgaaac ccagaatggt cggccaggcg      60
gattagtttt ggagtactcg ctcc                                            84

<210> SEQ ID NO 2
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggagggaaaa gttatcaggc caagcacaag aactttcaaa acgcagaatg ctgggcttgg      60
gattagtttt ggagtactcg ctcc                                            84

<210> SEQ ID NO 3
<211> LENGTH: 84

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggagggaaaa gttatcaggc cagacgagaa tttggaaaac gcggaacgcc gtctggtgtg        60
gattagtttt ggagtactcg ctcc                                               84

<210> SEQ ID NO 4
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggagggaaaa gttatcaggc atcacgtggt gggcaaataa ccggttgggg tgggtcgagg        60
gattagtttt ggagtactcg ctcc                                               84

<210> SEQ ID NO 5
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggagggaaaa gttatcaggc aacgggaaga aatgtcgaaa cccttgaaag gtcacggact        60
gattagtttt ggagtactcg ctcc                                               84

<210> SEQ ID NO 6
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggagggaaaa gttatcaggc cactgcgggg gtctatacgt gaggaagaag tgggcaggtc        60
gattagtttt ggagtactcg ctcc                                               84

<210> SEQ ID NO 7
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggagggaaaa gttatcaggc gcaagtatga gcgcaggagt taggtcccgt ggcgatgggt        60
gattagtttt ggagtactcg ctcc                                               84

<210> SEQ ID NO 8
<211> LENGTH: 83
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 8
ggagggaaaa gttatcaggc gtaggtgggg gactggggac gggtatgggc acacggtatg    60
attagttttg gagtactcgc tcc    83

<210> SEQ ID NO 9
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggagggaaaa gttatcaggc gacgttaagc tagcaggtgt taggtcccgt ggtgatgaat    60
gattagtttt ggagtactcg ctcc    84

<210> SEQ ID NO 10
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggagggaaaa gttatcaggc gggaggagaa ttaataaaaa cccgggacgg ccgacgggat    60
gattagtttt ggagtactcg ctcc    84

<210> SEQ ID NO 11
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggagggaaaa gttatcaggc cagaacaaag cgggagaatt atgaaaacgc ggaacgccac    60
gattagtttt ggagtactcg ctcc    84

<210> SEQ ID NO 12
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggagggaaaa gttatcaggc gctaagagaa atatcgaaac cctggatagg ctgagtgact    60
gattagtttt ggagtactcg ctcc    84

<210> SEQ ID NO 13
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
ggagggaaaa gttatcaggc aggtgtaggc cctgtggtga tgaatcgcgt gtcgaggggt      60
gattagtttt ggagtactcg ctcc                                            84
```

<210> SEQ ID NO 14
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
ggagggaaaa gttatcaggc cgcagcggag aaatttcgaa acccaggatg gccgcgaggt      60
gattagtttt ggagtactcg ctcc                                            84
```

<210> SEQ ID NO 15
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
ggagggaaaa gttatcaggc gacgggacga aaaacggttg gatgaggttg gttgggtgtg      60
gattagtttt ggagtactcg ctcc                                            84
```

<210> SEQ ID NO 16
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
ggagggaaaa gttatcaggc taaaccccaa aacagtgcaa ctaggtgtag gtcccgtggt      60
gattagtttt ggagtactcg ctcc                                            84
```

<210> SEQ ID NO 17
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
ggagggaaaa gttatcaggc ggccagagaa atgtcgaaac ccggtaacgg atggtaagct      60
gattagtttt ggagtactcg ctcc                                            84
```

<210> SEQ ID NO 18
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
ggagggaaaa gttatcaggc cagccactgg agaaagtaag aaacgcagaa tgcccagtgg      60
gattagtttt ggagtactcg ctcc                                            84
```

<210> SEQ ID NO 19
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggagggaaaa gttatcaggc acggactcgc aaaaggtgga acaggagtgg gccccgcggc      60
gattagtttt ggagtactcg ctcc                                            84

<210> SEQ ID NO 20
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggagggaaaa gttatcaggc tgcggcgaga aatgtcgaaa cggtgaaacc cgccatgcgt      60
gattagtttt ggagtactcg ctcc                                            84

<210> SEQ ID NO 21
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggagggaaaa gttatcaggc cacccgtcag gggttcgttg tgaggagaga gggttgggcc      60
gattagtttt ggagtactcg ctcc                                            84

<210> SEQ ID NO 22
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggagggaaaa gttatcaggc cgagtgaaag aggcaggtgt aggtcccgtg gaggtcaggt      60
gattagtttt ggagtactcg ctcc                                            84

<210> SEQ ID NO 23
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggagggaaaa gttatcaggc aggcgcgaga aatatcgaaa caccggacgg tcgcgacgct      60
gattagtttt ggagtactcg ctcc                                            84

<210> SEQ ID NO 24
<211> LENGTH: 84
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 24
ggagggaaaa gttatcaggc agagggagg gtcgggtatc ggcgtgttcg ggggatctgc    60
gattagtttt ggagtactcg ctcc    84

<210> SEQ ID NO 25
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
ggagggaaaa gttatcaggc ccgggagaat tagattaaaa cgcggaacgc cccgtgcccg    60
gattagtttt ggagtactcg ctcc    84

<210> SEQ ID NO 26
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
ggagggaaaa gttatcaggc agtgtaggga gcggagtagg caggcgtagg tcctgtggtg    60
attagttttg gagtactcgc tcc    83

<210> SEQ ID NO 27
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ggagggaaaa gttatcaggc ggcgttgtcg ggcgcaggtg taggcctcgt ggtggtgggt    60
gattagtttt ggagtactcg ctcc    84

<210> SEQ ID NO 28
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
ggagggaaaa gttatcaggc gggggacaag ggtcgggtat gggcgcctcg agaactgggt    60
gattagtttt ggagtactcg ctcc    84

<210> SEQ ID NO 29
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
ggagggaaaa gttatcaggc ataggcaacg gggatgataa ccagttgggg tgggacgagg    60
gattagtttt ggagtactcg ctcc    84

<210> SEQ ID NO 30
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggagggaaaa gttatcaggc tgcggaaggt aggttatacg agcgcgcagg actggtaata    60
gattagtttt ggagtactcg ctcc    84

<210> SEQ ID NO 31
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggagggaaaa gttatcaggc agtgagaggt taaaggaagg gtgcgttgtc aaaggctggt    60
gattagtttt ggagtactcg ctcc    84

<210> SEQ ID NO 32
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggagggaaaa gttatcaggc gtaagcgaag ggtcaaaaag gccgagcggt ttaggcatca    60
gattagtttt ggagtactcg ctcc    84

<210> SEQ ID NO 33
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggagggaaaa gttatcaggc taaaccccaa aacagtgcaa ctaggtgtag gtcccgtggt    60
gattagtttt ggagtactcg ctcc    84

<210> SEQ ID NO 34
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggagggaaaa gttatcaggc ccggcttcga agggtgaata ctgagcggaa gtgagaggaa    60

```
gattagtttt ggagtactcg ctcc                                              84
```

<210> SEQ ID NO 35
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
ggagggaaaa gttatcaggc gcaaggaggt aaaaggaagg gtggttgctt ggcgctaacg        60
gattagtttt ggagtactcg ctcc                                              84
```

<210> SEQ ID NO 36
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
ggagggaaaa gttatcaggc gtaatggaag ggcgttatga acgctgagcg cattagggt         60 gattagtttt ggagtactcg ctcc                                              84
```

<210> SEQ ID NO 37
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
ggagggaaaa gttatcaggc ctagtgttat gaccctagaa atagatgagt tgagaggtcg        60
gattagtttt ggagtactcg ctcc                                              84
```

<210> SEQ ID NO 38
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
ggagggaaaa gttatcaggc gcatgtgaag ggaccaatcc gagcgacatg gtgcgggata        60
gattagtttt ggagtactcg ctcc                                              84
```

<210> SEQ ID NO 39
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39

```
ggagggaaaa gttatcaggc tatggaaggg atagggtatc cgagcgcaga ggctgaggat        60
tagttttgga gtactcgctc c                                                 81
```

```
<210> SEQ ID NO 40
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggagggaaaa gttatcaggc atagaggtga gaggaagggt gtgttgtatg ttgataacga      60
gattagtttt ggagtactcg ctcc                                            84

<210> SEQ ID NO 41
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggagggaaaa gttatcaggc tcacgaagtc agcaataatt tgctgtaggc ggtggggact      60
gattagtttt ggagtactcg ctcc                                            84

<210> SEQ ID NO 42
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggagggaaaa gttatcaggc acgtagtggg aggacgcgga aagtcgagcg cattaggtgg      60
gattagtttt ggagtactcg ctcc                                            84

<210> SEQ ID NO 43
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggagggaaaa gttatcaggc gcggtggaag gctgaacatt ggcgagcgca tcggagatct      60
gattagtttt ggagtactcg ctcc                                            84

<210> SEQ ID NO 44
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggagggaaaa gttatcaggc cagagaaaca taaaccataa acgcagaagc tggctgtgag      60
gattagtttt ggagtactcg ctcc                                            84

<210> SEQ ID NO 45
<211> LENGTH: 84
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 45
ggagggaaaa gttatcaggc gttcttgtag tgcatccaat tgcagagcga aggaggtgtt     60
gattagtttt ggagtactcg ctcc                                            84

<210> SEQ ID NO 46
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
ggagggaaaa gttatcaggc acgtagttga aggactttttg ggttgagcgg actaggtgta    60
gattagtttt ggagtactcg ctcc                                            84

<210> SEQ ID NO 47
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
ggagggaaaa gttatcaggc aatgacatat ttcttatatc gggtttggag tgccttgcct     60
agattagttt tggagtactc gctcc                                           85

<210> SEQ ID NO 48
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
ggagggaaaa gttatcaggc aatgacattt tcttatatcg ggtttggagt gccctgccta     60
gattagtttt ggagtactcg ctcc                                            84

<210> SEQ ID NO 49
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
ggagggaaaa gttatcaggc atgtattgcg gatgattttg tatttaatgt gtatgcctcg     60
gattagtttt ggagtactcg ctcc                                            84

<210> SEQ ID NO 50
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

```
<400> SEQUENCE: 50
ggagggaaaa gttatcaggc cggggtgggg agtaacaggc tgttggtagg ggtggacctg      60
gattagtttt ggagtactcg ctcc                                             84

<210> SEQ ID NO 51
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggagggaaaa gttatcaggc aaaggagaag gtccaaaacg gcctgggtgg tgggtatgtg      60
gattagtttt ggagtactcg ctcc                                             84

<210> SEQ ID NO 52
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggagggaaaa gttatcaggc tggatggtag ctcggtcggg gtgggtgggt tggcaagtct      60
gattagtttt ggagtactcg ctcc                                             84

<210> SEQ ID NO 53
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggagggaaaa gttatcaggc gagtgcgtaa tggtacgatt tgggaagtgg cttggggtgg      60
gattagtttt ggagtactcg ctcc                                             84

<210> SEQ ID NO 54
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggagggaaaa gttatcaggc aaaggagaag gctcaaaacg gcctgggtgg tgggtatgtg      60
gattagtttt ggagtactcg ctcc                                             84

<210> SEQ ID NO 55
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggagggaaaa gttatcaggc ggatacagca gaataaggga aggggcagat cggggtgggg      60
```

```
attagttttg gagtactcgc tcc                                           83
```

<210> SEQ ID NO 56
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 56

```
ggagggaaaa gttatcaggc agcaaacagc aggtagaggg aagtggcaga tcggggtggg   60
gattagtttt ggagtactcg ctcc                                          84
```

<210> SEQ ID NO 57
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 57

```
ggagggaaaa gttatcaggc gagcggggac gaacacatat ggggaagtgg cttggggtgg   60
gattagtttt ggagtactcg ctcc                                          84
```

<210> SEQ ID NO 58
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 58

```
ggagggaaaa gttatcaggc gagtgcgtaa tggtacgatt tgggaagtgg tttggggtgg   60
gattagtttt ggagtactcg ctcc                                          84
```

<210> SEQ ID NO 59
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 59

```
ggagggaaaa gttatcaggc cgacagtggg tagcggttaa ggggaagtgg cttggggtgg   60
gattagtttt ggagtactcg ctcc                                          84
```

<210> SEQ ID NO 60
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 60

```
ggagggaaaa gttatcaggc cggggtggga taaaagcatg gttggtaggg gttggggcat   60
gattagtttt ggagtactcg ctcc                                          84
```

<210> SEQ ID NO 61

<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggagggaaaa gttatcaggc aaggcgtgtg tatccctgtg gtaggggttg gtcggggtgg      60
gattagtttt ggagtactcg ctcc                                            84

<210> SEQ ID NO 62
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggagggaaaa gttatcaggc cagggtcggg attgggcggg gtctggaaga tcatgtgcca      60
gattagtttt ggagtactcg ctcc                                            84

<210> SEQ ID NO 63
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggagggaaaa gttatcaggc cggggggga agacgagtgt aagttggtag ggtggggtag       60
gattagtttt ggagtactcg ctcc                                            84

<210> SEQ ID NO 64
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccactgcggg ggtctatacg tgaggaagaa gtgggcaggt cgagtgcgta atggtacgat      60
ttgggaagtg gcttggggtg gg                                              82

<210> SEQ ID NO 65
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gagtgcgtaa tggtacgatt tgggaagtgg cttggggtgg gccactgcgg ggtctatac      60 gtgaggaaga agtgggcagg tc                                              82

<210> SEQ ID NO 66
<211> LENGTH: 97
<212> TYPE: DNA
<213> ORGANISM: Artificial Sequence
<220> FEATURE:

<223> OTHER INFORMATION: Description of Artificial Sequence: Synthetic
    oligonucleotide

<400> SEQUENCE: 66
ccactgcggg ggtctatacg tgaggaagaa gtgggcaggt caaaaaaaaa aaaaaagagt    60
gcgtaatggt acgatttggg aagtggcttg gggtggg    97

<210> SEQ ID NO 67
<211> LENGTH: 120
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 67
ccactgcggg ggtctatacg tgaggaagaa gtgggcaggt caaaaaaaaa aaaaaagagt    60
gcgtaatggt acgatttggg aagtggcttg gggtgggatt agttttggag tactcgctcc    120

<210> SEQ ID NO 68
<211> LENGTH: 113
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 68
ccactgcggg ggtctatacg tgaggaagaa gtggaaaaaa aaaaaaaaag agtgcgtaat    60
ggtacgattt gggaagtggc ttggggtggg attagttttg gagtactcgc tcc    113

<210> SEQ ID NO 69
<211> LENGTH: 97
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 69
gagtgcgtaa tggtacgatt tgggaagtgg cttggggtgg gaaaaaaaaa aaaaaaccac    60 tgcggggtc tatacgtgag gaagaagtgg gcaggtc    97

<210> SEQ ID NO 70
<211> LENGTH: 41
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: 3'-iSp9

<400> SEQUENCE: 70
ccactgcggg ggtctatacg tgaggaagaa gtgggcaggt c    41

<210> SEQ ID NO 71
<211> LENGTH: 41
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: 3'-iSp9

<400> SEQUENCE: 71
gagtgcgtaa tggtacgatt tgggaagtgg cttggggtgg g         41

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-iSp18

<400> SEQUENCE: 72
ccactgcggg ggtctatacg tgaggaagaa gtgggcaggt c         41

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-iSp18

<400> SEQUENCE: 73
gagtgcgtaa tggtacgatt tgggaagtgg cttggggtgg g         41

<210> SEQ ID NO 74
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
ggagggaaaa gttatcaggc cactgcgggg gtctatacgt gaggaagaag tgggcaggtc      60
gattagtttt ggagtactcg ctccggaggg aaaagttatc aggctggatg gtagctcggt     120
cggggtgggt gggttggcaa gtctgattag ttttggagta ctcgctcc                  168

<210> SEQ ID NO 75
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
ggagggaaaa gttatcaggc tggatggtag ctcggtcggg gtgggtgggt tggcaagtct      60
gattagtttt ggagtactcg ctccggaggg aaaagttatc aggccactgc ggggtctat     120 acgtgaggaa gaagtgggca ggtcgattag ttttggagta ctcgctcc                  168

<210> SEQ ID NO 76
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
ccactgcggg ggtctatacg tgaggaagaa gtgggcaggt cgattagttt tggagtactc      60
gctccggagg gaaaagttat caggctggat ggtagctcgg tcggggtggg tgggttggca     120
agtctgatta gttttggagt actcgctcc                                       149
```

<210> SEQ ID NO 77
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
ccactgcggg ggtctatacg tgaggaagaa gtgggcaggt cgattagttt tggagtactc      60
gctccggagg gaaaagttat caggcgagtg cgtaatggta cgatttggga agtggcttgg     120
ggtgggatta gttttggagt actc                                            144
```

<210> SEQ ID NO 78
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
gagtgcgtaa tggtacgatt tgggaagtgg cttggggtgg gattagtttt ggagtactcg      60
ctccggaggg aaaagttatc aggccactgc ggggtctat acgtgaggaa gaagtgg         117
```

<210> SEQ ID NO 79
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-C7-NH2

<400> SEQUENCE: 79

```
ggagggaaaa gttatcaggc tggatggtag ctcggtcggg gtgggtgggt tggcaagtct      60
gattagtttt ggagtactcg ctcc                                             84
```

<210> SEQ ID NO 80
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
ggagggaaaa gttatcaggc agagggagg gtcgggtatc ggcgtgttcg ggggatctgc       60
gattagtttt ggagtactcg ctccggaggg aaaagttatc aggctggatg gtagctcggt    120
cggggtgggt gggttggcaa gtctgattag ttttggagta ctcgctcc                  168
```

<210> SEQ ID NO 81
<211> LENGTH: 148
<212> TYPE: DNA
<213> ORGANISM: Artificial Sequence
<220> FEATURE:

<223> OTHER INFORMATION: Description of Artificial Sequence: Synthetic
       polynucleotide

<400> SEQUENCE: 81
gagtgcgtaa tggtacgatt tgggaagtgg cttggggtgg gattagtttt ggagtactcg    60
ctccggaggg aaaagttatc aggcagaggg gagggtcggg tatcggcgtg ttcggggat   120 ctgcgattag ttttggagta ctcgctcc                                     148

<210> SEQ ID NO 82
<211> LENGTH: 125
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 82
ccactgcggg ggtctatacg tgaggaagaa gtgggcaggt cggagggaaa agttatcagg    60
ctggatggta gctcggtcgg ggtgggtggg ttggcaagtc tgattagttt tggagtactc   120
gctcc                                                              125

<210> SEQ ID NO 83
<211> LENGTH: 107
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 83
ccactgcggg ggtctatacg tgaggaagaa gtgggcaggt catcaggcga gtgcgtaatg    60
gtacgatttg ggaagtggct tggggtggga ttagttttgg agtactc                107

<210> SEQ ID NO 84
<211> LENGTH: 116
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 84
ccactgcggg ggtctatacg tgaggaagaa gtgggcaggt caaaaaaaaa aaaaaaggag    60
ggaaaagtta tcaggctgga tggtagctcg gtcggggtgg gtgggttggc aagtct      116

<210> SEQ ID NO 85
<211> LENGTH: 101
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 85
ccactgcggg ggtctatacg tgaggaagaa gtgggcaggt cggagggaaa agttatcagg    60
ctggatggta gctcggtcgg ggtgggtggg ttggcaagtc t                      101

<210> SEQ ID NO 86
<211> LENGTH: 140
<212> TYPE: DNA
<213> ORGANISM: Artificial Sequence
<220> FEATURE:

<223> OTHER INFORMATION: Description of Artificial Sequence: Synthetic
     polynucleotide

<400> SEQUENCE: 86
ccactgcggg ggtctatacg tgaggaagaa gtgggcaggt caaaaaaaaa aaaaaaggag    60
ggaaaagtta tcaggctgga tggtagctcg gtcggggtgg gtgggttggc aagtctgatt   120
agttttggag tactcgctcc                                               140

<210> SEQ ID NO 87
<211> LENGTH: 133
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 87
ccactgcggg ggtctatacg tgaggaagaa gtggaaaaaa aaaaaaaaag gagggaaaag    60
ttatcaggct ggatggtagc tcggtcgggg tgggtgggtt ggcaagtctg attagttttg   120
gagtactcgc tcc                                                      133

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
     6xHis tag

<400> SEQUENCE: 88

His His His His His His
1               5

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
     10xHis tag

<400> SEQUENCE: 89

His His His His His His His His His His
1               5                   10

<210> SEQ ID NO 90
<211> LENGTH: 41
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: 5'-iSp9

<400> SEQUENCE: 90
gagtgcgtaa tggtacgatt tgggaagtgg cttggggtgg g                        41

<210> SEQ ID NO 91
<211> LENGTH: 41
<212> TYPE: DNA
<213> ORGANISM: Artificial Sequence
<220> FEATURE:
<223> OTHER INFORMATION: Description of Artificial Sequence: Synthetic
     oligonucleotide

```
<220> FEATURE:
<223> OTHER INFORMATION: 5'-iSp9

<400> SEQUENCE: 91
ccactgcggg ggtctatacg tgaggaagaa gtgggcaggt c                          41

<210> SEQ ID NO 92
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-iSp18

<400> SEQUENCE: 92
gagtgcgtaa tggtacgatt tgggaagtgg cttggggtgg g                          41

<210> SEQ ID NO 93
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-iSp18

<400> SEQUENCE: 93
ccactgcggg ggtctatacg tgaggaagaa gtgggcaggt c                          41

<210> SEQ ID NO 94
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-C3-SH

<400> SEQUENCE: 94
gttatcaggc cactgcgggg gtctatacgt gaggaagaag tgggcaggtc                 50

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcaggtcaaa aaaaaaaaaa aa                                               22

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aaaaaaaaaa aaaaa                                                       15
```

```
<210> SEQ ID NO 97
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gcaggtcgat tagttttgga gtactcgctc c                                          31

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggagggaaaa gttatcagg                                                        19

<210> SEQ ID NO 99
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcaggtcgat tagttttgga gtactcgctc cggagggaaa agttatcagg c                    51

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gctccggagg gaaaagttat cagg                                                  24

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gattagtttt ggagtactc                                                        19

<210> SEQ ID NO 102
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
attagttttg gagtactcgc tccggaggga aagttatca ggc                              43

<210> SEQ ID NO 103
```

```
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Biotin

<400> SEQUENCE: 103
ggagggaaaa gttatcaggc tggatggtag ctcggtcggg gtgggtgggt tggcaagtct    60
gattagtttt ggagtactcg ctcc                                          84

<210> SEQ ID NO 104
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gaaaagttat caggctggat ggtagctcgg tcggggtggg tgggttggca agtctgatta    60
gttttggagt actcgctcc                                                79

<210> SEQ ID NO 105
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
agttatcagg ctggatggta gctcggtcgg ggtgggtggg ttggcaagtc tgattagttt    60
tggagtactc gctcc                                                    75

<210> SEQ ID NO 106
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
atcaggctgg atggtagctc ggtcggggtg ggtgggttgg caagtctgat tagttttgga    60
gtactcgctc c                                                        71

<210> SEQ ID NO 107
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggctggatgg tagctcggtc ggggtgggtg ggttggcaag tctgattagt tttggagtac    60
tcgctcc                                                             67

<210> SEQ ID NO 108
<211> LENGTH: 64
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 108
tggatggtag ctcggtcggg gtgggtgggt tggcaagtct gattagtttt ggagtactcg    60
ctcc                                                                 64

<210> SEQ ID NO 109
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
ggagggaaaa gttatcaggc tggatggtag ctcggtcggg gtgggtgggt tggcaagtct    60
gattagtttt ggagtactc                                                 79

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
ggagggaaaa gttatcaggc tggatggtag ctcggtcggg gtgggtgggt tggcaagtct    60

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
tggatggtag ctcggtcggg gtgggtgggt tggcaagtct                          40

<210> SEQ ID NO 112
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gagtgcgtaa cggtatgact tgggaagtgg cttggggtgg g                        41

<210> SEQ ID NO 113
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
gaaaagttat caggcgagtg cgtaatggta cgatttggga agtggcttgg ggtgggatta    60
gttttggagt actcgctcc                                                 79

<210> SEQ ID NO 114
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gagtgcgtaa tggtacgatt tgggaagtgg cttggggtgg gattagttttt ggagtactcg    60 ctcc                                                                  64

<210> SEQ ID NO 115
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggagggaaaa gttatcaggc gagtgcgtaa tggtacgatt tgggaagtgg cttggggtgg    60
gattagtttt ggagtactc                                                  79

<210> SEQ ID NO 116
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Biotin

<400> SEQUENCE: 116
gagtgcgtaa tggtacgatt tgggaagtgg cttggggtgg gattagtttt ggagtactc     59

<210> SEQ ID NO 117
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gagtgcgtaa tggtacgatt tgggaagtgg cttggggtgg gattagtttt gg            52

<210> SEQ ID NO 118
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gagtgcgtaa tggtacgatt tgggaagtgg cttggggtgg gattag                    46

<210> SEQ ID NO 119
<211> LENGTH: 41
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 119
gagtgcgtaa tggtacgatt tgggaagtgg cttggggtgg g    41

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gagtgcgtaa tggtacgatt tgggaagtgg cttggggtgg    40

<210> SEQ ID NO 121
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
atggtacgat ttgggaagtg gcttggggtg gg    32

<210> SEQ ID NO 122
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gaaaagttat caggccactg cgggggtcta tacgtgagga agaagtgggc aggtcgatta    60
gttttggagt actcgctcc    79

<210> SEQ ID NO 123
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cactgcgggg gtctatacgt gaggaagaag tgggcaggtc gattagtttt ggagtactcg    60
ctcc    64

<210> SEQ ID NO 124
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ggagggaaaa gttatcaggc cactgcgggg gtctatacgt gaggaagaag tgggcaggtc    60
gattagtttt ggagtactc    79

<210> SEQ ID NO 125

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggagggaaaa gttatcaggc cactgcgggg gtctatacgt gaggaagaag tgggcaggtc    60

<210> SEQ ID NO 126
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Biotin

<400> SEQUENCE: 126
gaaaagttat caggccactg cggggtcta tacgtgagga agaagtgggc aggtc    55

<210> SEQ ID NO 127
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
caggccactg cggggtcta tacgtgagga agaagtgggc aggtc    45

<210> SEQ ID NO 128
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ccactgcggg ggtctatacg tgaggaagaa gtgggcaggt c    41

<210> SEQ ID NO 129
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cactgcgggg gtctatacgt gaggaagaag tgggcaggtc    40

<210> SEQ ID NO 130
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ccactgcggg ggtctatacg tgaggaagaa gtgg    34

```
<210> SEQ ID NO 131
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Biotin

<400> SEQUENCE: 131
ggagggaaaa gttatcaggc agaggggagg gtcgggtatc ggcgtgttcg ggggatctgc      60
gattagtttt ggagtactcg ctcc                                            84

<210> SEQ ID NO 132
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aaagttatca ggcagagggg agggtcgggt atcggcgtgt tcggggatc tgcgattagt      60 tttggagtac tcgctcc                                                    77

<210> SEQ ID NO 133
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tcaggcagag gggagggtcg ggtatcggcg tgttcggggg atctgcgatt agttttggag      60
tactcgctcc                                                            70

<210> SEQ ID NO 134
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agaggggagg gtcgggtatc ggcgtgttcg ggggatctgc gattagtttt ggagtactcg      60
ctcc                                                                  64

<210> SEQ ID NO 135
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ggagggaaaa gttatcaggc agaggggagg gtcgggtatc ggcgtgttcg ggggatctgc      60
gattagtttt ggagta                                                     76

<210> SEQ ID NO 136
<211> LENGTH: 68
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggagggaaaa gttatcaggc agaggggagg gtcgggtatc ggcgtgttcg ggggatctgc      60
gattagtt                                                              68

<210> SEQ ID NO 137
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggagggaaaa gttatcaggc agaggggagg gtcgggtatc ggcgtgttcg ggggatctgc      60
```

BISPECIFIC APTAMERS MEDIATING TUMOUR CELL LYSIS

Sequence Listing The instant application contains a Sequence Listing which has been submitted in ASCII format via EFS-Web and is hereby incorporated by reference in its entirety. Said ASCII copy, created on Jun. 12, 2013, is named MERCK-4083_SL.txt and is 41,619 bytes in size.

Aptamers are single stranded DNA or RNA oligonucleotides that can bind molecules of nearly all classes. Their defined and rigid tertiary structure allows a both specific and highly affine molecular recognition of various targets. They can vary from 15 to 85 nucleotides in length resulting in apparent molecular mass of 5-25 kDa.

Aptamers are found by a process referred to as SELEX, selecting on either isolated recombinant protein ("filter SELEX") or whole cells ("cell SELEX")

Several characteristics offer specific competitive advantages of aptamers over antibodies and other protein-based formats:
- a supposed absence of immunogenicity. Aptamers display low to no immunogenicity when administered in pre-clinical doses 1000-fold greater than doses used in animal and human therapeutic applications. Whereas the efficacy of many monoclonal antibodies can be severely limited by immune responses against antibodies themselves, it is extremely difficult to elicit antibodies to aptamers, most likely because aptamers cannot be presented by T-cells via MHC and the immune response is generally not trained to recognise extra-cellular nucleic acids.
- a facile and putatively cost-effective production by chemical synthesis with high accuracy and reproducibility. No variation between different production charges is anticipated. They are purified by stringent, denaturing conditions ensuring very high purity.
- a high affinity and selectivity is achievable. Therapeutic aptamers are chemically robust. Aptamers denatured by heat or denaturants intrinsically regenerate easily within minutes and can be stored for extended periods up to one year at room temperature as lyophilized powders, thus exhibit a very high shelf-life. Heat- and nuclease-resistant when modified.
- a good solubility (>150 mg/mL) and comparatively low molecular weight (aptamer: 10-50 kDa to antibody: 150 kDa).

The SELEX™ Method

Figure 2:
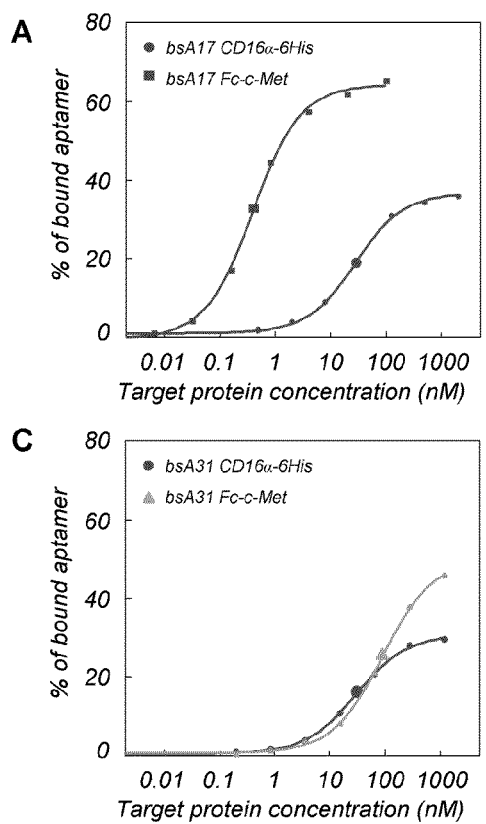

A suitable method for generating an aptamer is with the process entitled "Systematic Evolution of Ligands by Exponential Enrichment" ("SELEX™") generally depicted in FIG. 2. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand, i.e., each aptamer, is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX™ relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed and/or conserved sequence incorporated within randomized sequence. In other examples, the pool comprises random or partially random oligonucleotides containing at least one fixed and/or conserved sequence at its 5' and/or 3' end which may comprise a sequence shared by all the molecules of the oligonucleotide pool. Fixed sequences are sequences such as hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g., U.S. Pat. Nos. 5,958,691; 5,660,985; 5,958,691; 5,698,687; 5,817,635; 5,672,695, and PCT Publication WO 92/07065. Random oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield 1014-1016 individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be either RNA or DNA. In those instances where an RNA library is to be used as the starting library it is typically generated by transcribing a DNA library in vitro using T7 RNA polymerase or modified T7 RNA polymerases and purified. The RNA or DNA library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have 420 candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately 1014 different nucleic acid species but may be used to sample as many as about 1018 different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides and in some embodiments of about 30 to about 40 nucleotides. In one example, the 5'-fixed:random:3'-fixed sequence comprises a random sequence of about 30 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photoreactive groups capable of binding and/or photocrosslinking to and/or photo-inactivating a target molecule. U.S. Pat. Nos. 5,567,588 and 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; e) contacting the increased affinity nucleic acids with one or more non-target molecules such that nucleic acid ligands with specific affinity for the non-target molecule(s) are removed; and f) amplifying the nucleic acids with specific affinity only to the target molecule to yield a mixture of nucleic acids enriched for nucleic acid sequences with a relatively higher affinity and specificity for binding to the target molecule. As described above for SELEX™, cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-NH2), 2'-fluoro(2'-F), and/or 2'-OMe (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanidine. Modifications can also include 3' and 5' modifications such as capping.

Further methods useful for the selection and identification of aptamers are e.g. detailed in U.S. Pat. No. 7,803,931 which is herewith incorporated by reference.

The aptamers of the present invention may consist of DNA, dRmY, rGmH, rRfY, dCmD, mRfY, MNA or rRnY compositions, with R=purine; Y=pyrimidine; H=A,C,U; D=A,G,U; d=2' deoxy; r=2' hydroxy; m=2' methoxy; f=2' fluoro; n=2' amine.

Therapeutic approaches to engage the intact but often hindered own immune system by enhanced recruitment of effector cell populations to the tumour are applied for several tumour related antigens (TRA) as well as effector specific antigens (ESA). One potent ESA amongst others is CD16 (FcγRIII) on natural killer (NK) cells and macrophages. Most bispecific approaches reported target CD3ε on Cytotoxic T-Lymphocytes (CTLs) or CD16α on natural killer cells. The proof of concept for recruitment of NK cells to tumour targets via bispecific binders was achieved with a bispecific single-chain Fv antibody against CD19 and CD16.

Antibody-dependent cellular cytotoxicity (ADCC) originating from the interaction of specific binding sites within the Fc-region of antibodies with Fcγ receptors (FcγR) plays a pivotal role in the therapy of various tumours. Specific polymorphisms at position 158 enhance FcγRIIIa affinity for IgG1 and are associated with improved ADCC and, as a result, in an improved clinical outcome in lymphoma patients.

CD16 is the only Fcγ receptor expressed on NK cells. Two Isoforms exist: CD16α and CD16β. CD16α is an intermediate affinity receptor for polyvalent immune-complexed IgG1 and IgG3, but not for IgG2 and IgG4. It is involved in phagocytosis, secretion of enzymes and inflammatory mediators, antibody-dependent cytotoxicity and clearance of immune complexes. In humans, it is a 50-70 kDa type I transmembrane activating receptor expressed by NK cells, δγ-T cells, monocytes, and macrophages. CD16α comes in two allotypes, differing in position 158. The V158 allotype exhibits higher affinity to the Fc region of antibodies.

FcγRIIIβ (CD16β) is highly related, sharing 97% amino acid sequence identity within the extracellular domain (ECD) with CD16α, but is a glycosyl-phosphatidyl-inositol-(GPI)-linked receptor expressed on human neutrophils and eosinophils.

The ECD of both CD16α and β can be proteolytically cleaved and retains binding activity in soluble form. The prevalent soluble isoform is neutrophil-derived sCD16β. The amount of sCD16α can be in healthy persons.

Hepatocyte growth factor receptor (HGFR) or c-Met is a membrane receptor tyrosine kinase that is essential for embryonic development and wound healing. It is normally expressed by cells of epithelial origin. It is nowadays recognized as a TRA. The primary single chain precursor protein is post-translationally cleaved to produce the alpha and beta subunits, which are disulfide linked to form the mature receptor. Upon stimulation by its ligand hepatocyte growth factor (HGF), c-Met induces several biological responses that collectively give rise to a program known as invasive growth.

Abnormal c-Met activation or over-expression in cancer correlates with poor prognosis, where aberrantly active c-Met MET [c-met?] triggers tumour growth, formation of new blood vessels (angiogenesis), and cancer spread to other organs (metastasis). c-Met is deregulated in many types of human malignancies, including cancers of kidney, liver, stomach, breast, and brain.

Further c-Met validation in cancer includes:
Over expression of both receptor and ligand in many tumour-types relative to surrounding tissue
Gene amplification observed in multiple indications
Introduction of c-Met into cell lines confers tumourgenicity and metastatic propensity
Inhibition of receptor/ligand function reverses cancer phenotypes (motility, invasion, proliferation and in vivo tumour growth)

There is no reliable therapy for many different types of cancers available. One example of such cancers are c-Met over expressing cancers.

It is therefore a preferred object of the present invention to provide a new therapy for treating such cancers, preferably cancers over expressing c-Met.

It has surprisingly been found by the present inventors that bispecific aptamer molecules directed to a TRA and an ESA provide an powerful means for cancer therapy.

An example of such a molecule is an aptamer bispecific for CD16α and c-Met. Another example would be an aptamer directed to CD16α and EGFR.

The type of tumour antigen useful in this invention may be a tumour-specific antigen (TSA) or a tumour-associated antigen (TAA). A TSA is unique to tumour cells and does not occur on other cells in the body. A TAA associated antigen is not unique to a tumour cell and instead is also expressed on a normal cell under conditions that fail to induce a state of immunologic tolerance to the antigen. The expression of the antigen on the tumour may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumour cells. TSAs and TAAs can be jointly referred to as TRA or a tumour related antigen.

Examples for TRAs are: MUC-1, PSMA, EGFR, Nucleolin, Sialyl Lewis X, PDGFR, VEGF and VEGFR, CD40, CD19, CD20, CD22, CD33, CD52, FAP, TR, CEA, GD2, Wue, melanoma proteoglycan, p glycoprotein, endoglin, HMW-MAA, ErbB1, HER1, HER2/neu, ErbB2, EpCAM, LewisY Examples for ESAs are CD32a/b (FcγRIIa/b), CD64 (FcγRI), CD16α on NK cells, CD3ε and CD28 on cytotoxic T-lymphocytes, CD89 (FcαRI) on Neutrophiles, Monocytes and Macrophage, DEC-250 on dendritic cells and C1q for complement activation.

A preferred TRA is c-Met. A further preferred TRA is EGFR

A preferred ESA is CD16α.

A very preferred aspect of the present invention is therefore the provision of aptamers selected from the group consisting of the aptamers set forth in SEQ ID NOs: 64-87 and 90-93, with SEQ ID NO: 82 and / or 87 being specially preferred.

So far, no DNA aptamers against CD16α or c-Met have been provided in the art.

It is a further object of the present invention to provide monospecific aptamers directed against TRAs. One preferred use of such monospecific aptamers directed against a TRA is the use as a building block in a bispecific aptamer of the invention.

Such monospecific aptamers against TRAs are e.g. directed against (i.e. binding to with high specificity with a Kd in the picomolar, more preferred nanomolar range): MUC-1, PSMA, EGFR, Nucleolin, Sialyl Lewis X, PDGFR, VEGF and VEGFR, CD40, CD19, CD20, CD22, CD33, CD52, FAP, TR, CEA, GD2, Wue, melanoma proteoglycan, p glycoprotein, endoglin, HMW-MAA, ErbB1, HER1, HER2/neu, ErbB2, EpCAM, LewisY.

Specially preferred aspects comprise monospecific aptamers against c-Met or EGFR, preferably c-Met.

Therefore the invention in very preferred aspect relates to one or more aptamers selected from the group of aptamers consisting of the aptamers disclosed in SEQ ID NOs: 50-63, wherein SEQ ID NO: 53 and/or 54 are specially preferred.

An equally important aspect of the present invention is to provide monospecific aptamers directed against ESAs. One preferred use of such monospecific aptamers directed against a ESA is the use as a building block in a bispecific aptamer of the invention.

Such monospecific aptamers against TRAs are e.g. directed against (i.e. binding to with high specificity with A Kd in the picomolar, more preferred nanomolar range): CD32a/b (FcγRIIa/b), CD64 (FcγRI), CD16α on NK cells, CD3ε and CD28 on cytotoxic T-lymphocytes, CD89 (FcαRI) on Neutrophiles, Monocytes and Macrophage, DEC-250 on dendritic cells and C1q for complement activation Specially preferred aspects comprise monospecific aptamers against CD16α.

Therefore the invention in very preferred aspect relates to one or more aptamers selected from the group of aptamers consisting of the aptamers disclosed in SEQ ID NOs: 1-49, wherein SEQ ID NO: 4, 6 and/or 24 are specially preferred.

The figures show the following:

FIG. 1: Sequence optimisation of aptamers: A, Removal of full flanking sequences of CLN0004 resulted in complete loss of binding in dot blot experiments (♦), whereas addition of only G61 (▲) recovered nearly similar affinity as the original clone (●). B, Removal of C20 in CLN0020 altered low nanomolar affinity (♦) to hardly any binding (▲) as determined in a dot blot. C, Minimisation of CLN0003 generally led to decrease of affinity, however still remaining in a low nanomolar range. Figure discloses SEQ ID NOS 52 and 103111, respectively, in order of appearance. D, Sequence variants of CLN0004 and 3' truncations exhibited lower affinities, while the 5' flanking sequence was not essential for c-Met binding. Figure discloses SEQ ID NOS 53, 58, and 112121, respectively, in order of appearance. E, CD16α aptamer CLN0020 was minimised to a 34mer core sequence while retaining a high affinity. Figure discloses SEQ ID NOS 6 and 122130, respectively, in order of appearance. F, Truncated CLN0123 constructs bound expectedly weak but with similar or improved affinities to CD16α. Figure discloses SEQ ID NOS 131137, respectively, in order of appearance. Intermittent, binding curves shifted due to temperature and protein batch variations; hence only direct, qualitative comparison to the original aptamer was feasible (indicated as ~11 nM in D).

FIG. 2: Dot blot binding curves of bispecific aptamers A and C, Dot blot binding curves of bispecific aptamers bsA17 and bsA31, respectively. Affinities to CD16 were comparable (19 and 24 nM) and in accordance with the parental-19nt-CLN0020-31nt (47nM). In contrast, CLN0003- derived bsA17 exhibited picomolar c-Met affinity (A) whereas CLN0004-derived bsA31 bound with 92 nM Kd to c-Met (C), reflecting the different affinities of parental aptamers CLN0003 and CLN0004 (91 pM and 57 nM, respectively). B, Dot blot derived affinities to CD16α and c-Met for all bispecific aptamers (except of bsA14 that was not produced). Generally, CLN0020retained original affinity when used 5', whereas c-Met aptamers performed best fused to the 3' end (bsA3, 5, 7 17-22). Linked full length aptamers yielded affinities similar to parental single aptamers (CLN0003: picomolar Kd of bsA9-11, 17, 21, 22; CLN0004: 18 nM of bsA12, 13; CLN0123: 174 nM and 178 nM of bsA15 and 16, respectively). bsA1 and bsA2 without linker exhibited a c-Met affinity decrease. Kd values are shown as mean values and standard deviation of independent dot blot experiments. Figures disclose "6His" as SEQ ID NO: 88.

Figure 3:
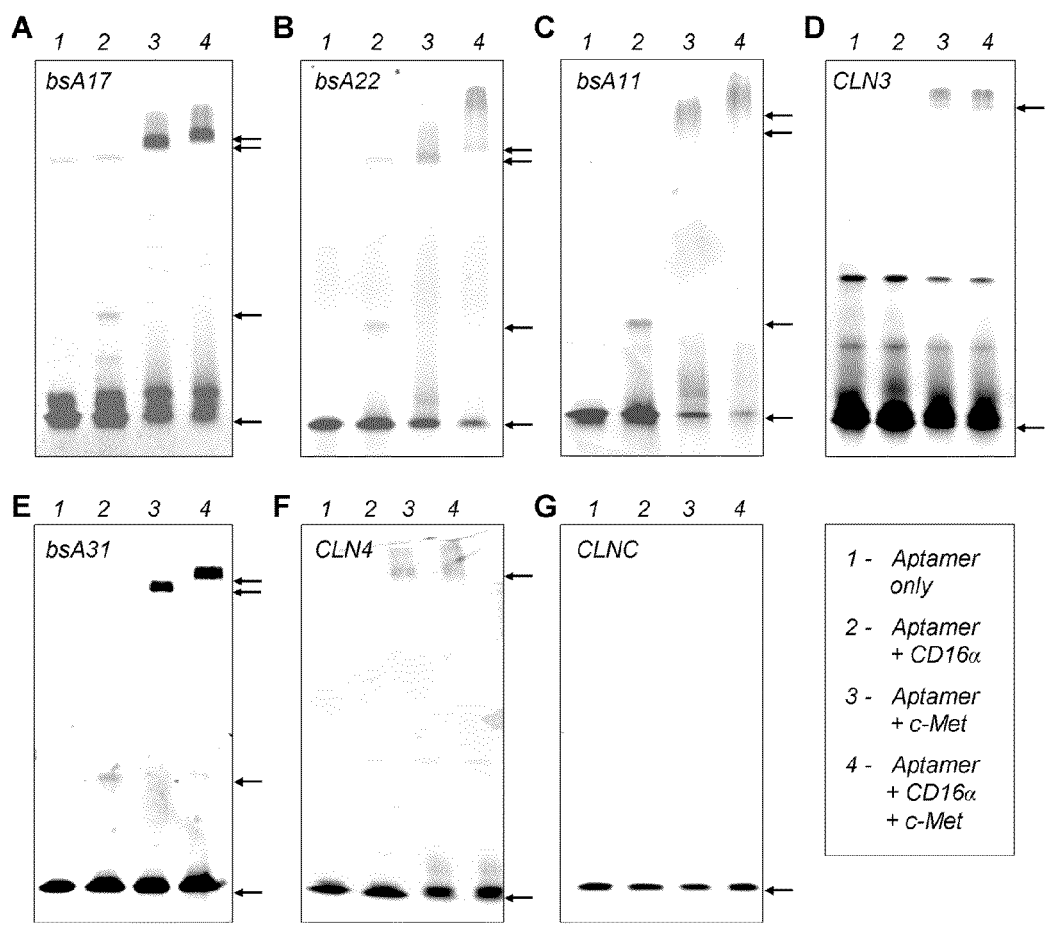

FIG. 3: Electrophoretic Motility Shift Assay (EMSA) to prove the simultaneous binding of both proteins (band shift of aptamer on TBE-gel when bound to both target proteins). A-C, CLN0003-derived bsA17, bsA22 and bsA11 all exhibited binding to CD16α-6His ("6His" disclosed as SEQ ID NO: 88) (additional band in lane 2) or c-Met-Fc fusion proteins (additional band in lane 3). This c-Met-Fc bound aptamer band shifted again upon addition of CD16α-6His_ ("6His" disclosed as SEQ ID NO: 88) (lane 4). D, Negative control parental single aptamer CLN0003, in contrast, did not show this migration shift. E and F, bsA31 and original single c-Met specific aptamer CLN0004 exhibited the same pattern, while non-binding negative control aptamer CLNC did not bind to any protein, as expected. Application of a gradient gel and size differences between CD16α-6His ("6His" disclosed as SEQ ID NO: 88and c-Met-Fc fusion protein led to differently extended migration (lanes 2 and 3) and an expectedly minor but clearly present migration shift upon addition of both target proteins (from lane 3 to 4). Arrows indicate the lowest migration frontier of specific aptamer bands. Weak additional bands in lanes 1 and 2 in A, B, C as well as all lanes in D could be due to unspecific aggregation.

Figure 4:
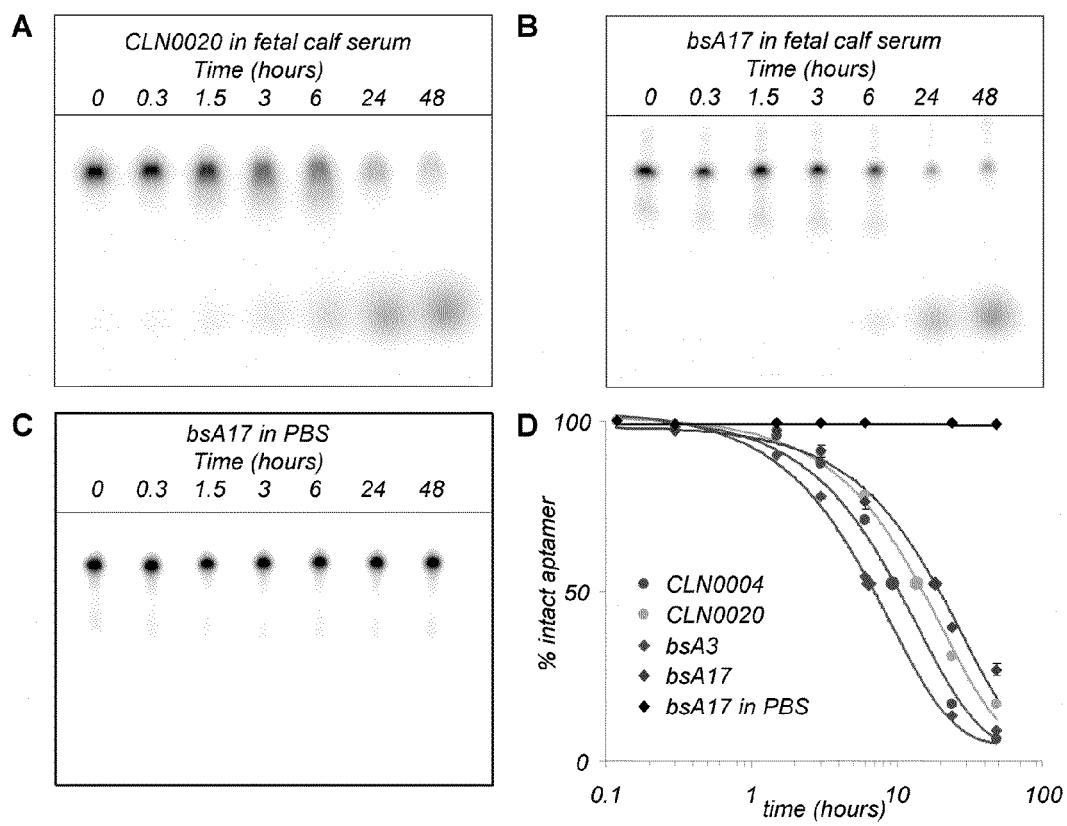
Figure 5:
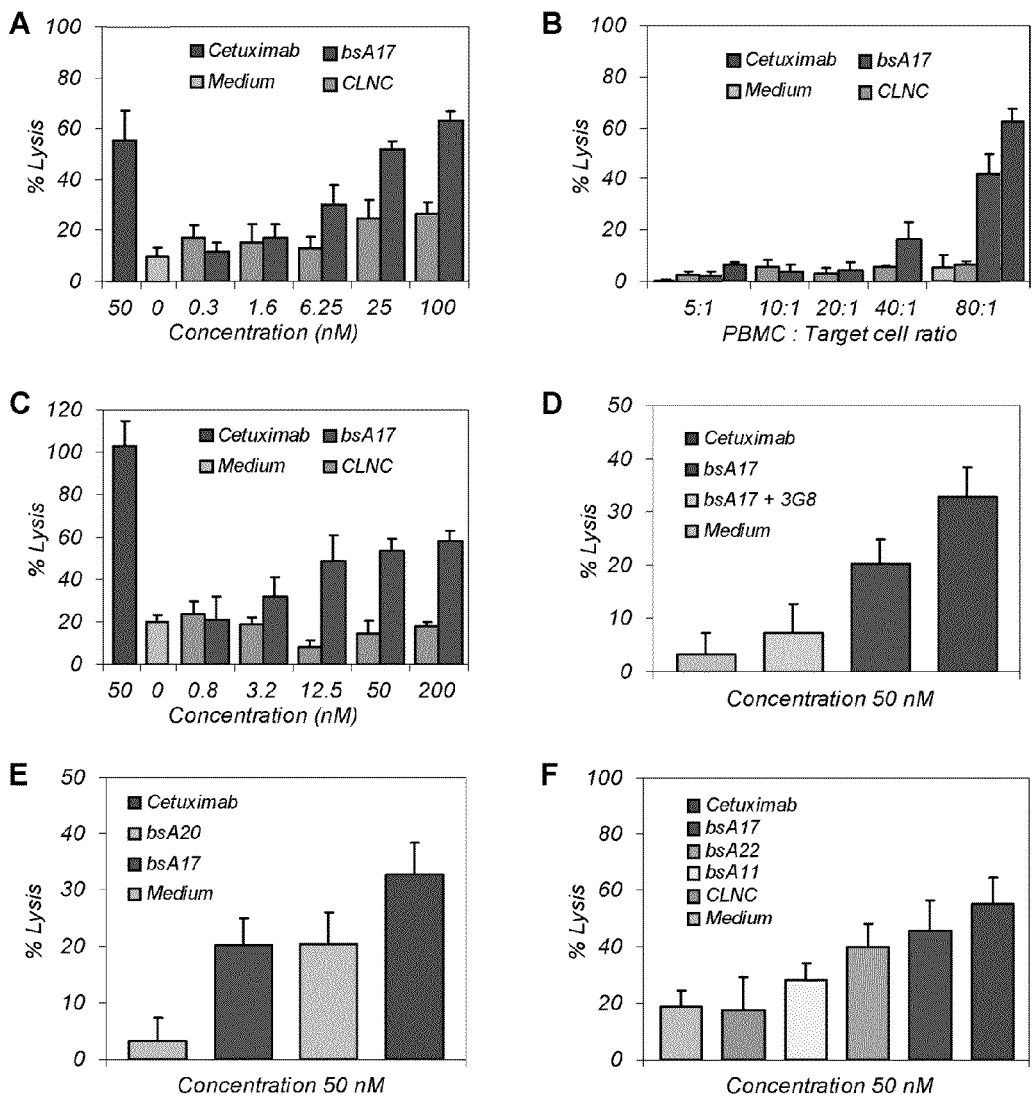

FIG. 4: Fetal Bovine Serum Stability for important single Aptamers (CLN0004, CLN0020) and bispecific constructs (bsA3 and bsA17). A and B, PAGE of CLN0020 or bsA17, respectively, after incubation in fetal calf serum at different time points. Bands at the migration level of the 0 h sample represented intact aptamer, while increasing signals at lower positions depicted breakdown products. C, bsA17 was stable in PBS over the whole time course, as debris could not be observed even after 48 h. D, Intensity values were extracted from gels as in A-C, the percentage of intact aptamer calculated and a curve fitted to the resulting time course. Half lives were determined as 6.4 h-20.3 h. Enlarged symbols indicate the half life fit of each aptamer FIG. 5: ADCC assay using bsA17 (SEQ ID NO: 82) A, Specific GTL-16 cell lysis mediated by bispecific aptamer bsA17 at a similar magnitude as cetuximab as positive control. Aptamer titration led to decrease of & lysis to background levels of non-binding negative control aptamer CLNC and reference with medium only. B, PBMC:target cell ratio reduction diminished specific GTL-16 cell lysis of both bsA17 and cetuximab at 50 nM. Note that the actual effector: target cell ratio was approximately 8:1 when applying 80:1 PBMC:target cells. C, bsA17 mediated concentration-dependent specific EBC-1 cell lysis as well analogously to GTL-16 target cells (A). D, Addition of 20-fold molar excess of antibody 3G8 resulted in a significant decrease of bsA17-mediated GTL-16 lysis due to inhibition of bsA17-binding to CD16α. E, Affinity differences of 352 pM (bsA17) to 5 nM (bsA20) showed no influence on effectiveness of GTL-16 cell lysis, whereas longer linker sequences (approximately bsA17 with 49 Å, bsA22 with 105 Å and bsA11 with 217 Å) led to a decrease of bsA-mediated GTL-16 cell lysis (F). Maximal lysis varied between individual experiments due to donor and CD16α allotype dependency. ADCC assays were performed 5 times with n=4 (A), 3 times with n=3 (B), 4 times with n=4 (C), 3 times with n=9 (D), 1 time with n=9 (E), 3 times with n=9 (F) and representative measurements are shown as calculated mean values, error bars indicate standard deviation.

Figure 6:
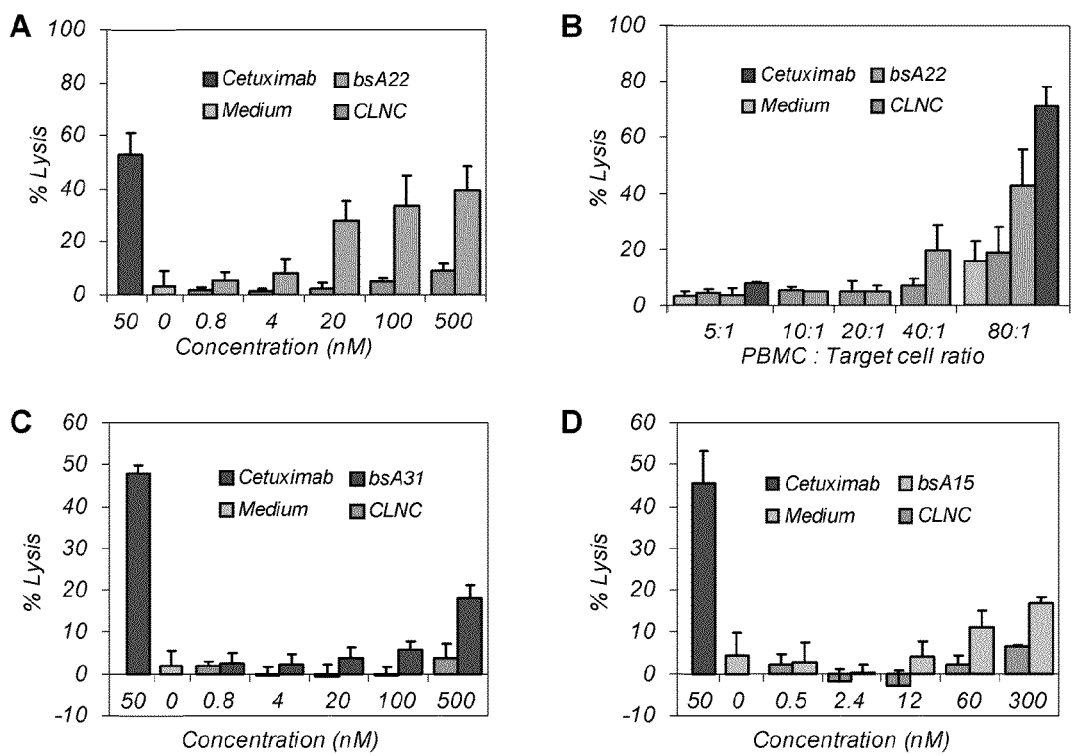

FIG. 6: ADCC assay using bsA22 (SEQ ID NO: 87) A, Bispecific aptamer bsA22 (SEQ ID NO: 87) induced specific tumour cell lysis in a concentration-dependent manner. bsA22 was nearly as potent as cetuximab with significantly higher lysis than non-binding aptamer control CLNC or medium reference. B, At 50 nM fixed concentration, both bsA22- and cetuximab-mediated lysis was diminished by reduction of PBMC:target cell ratio. C, Less c-Met affine bsA31 induced weaker but significant lysis at higher concentrations. D, bsA15, composed of CLN0123 as lower affinity CD16α binding entity, mediated weak but significant cytotoxicity as well. Human gastric adenocarcinoma GTL-16 cells applied in all measurements. Mean values with standard deviation are shown. Assays were performed in triplicate (B) or n=4-5 (A, C, D) 4 times (A), 1 time (B), 2 times (C) and 1 time (D) and representative measurements are shown.

In order to illustrate the invention, the following examples are included. However, it is to be understood that these examples do not limit the invention and are only meant to suggest a method of practicing the invention. Furthermore, the present examples are not to be construed to be limiting the invention, and the technical teaching of these examples may be combined with any technical teaching in the specification of the present application, as applicable to work the invention of bispecific aptamers for cancer treatment.

EXAMPLES

Example 1

Filter SELEX

Filter SELEX was based on the immobilisation of the target protein to a nitrocellulose membrane after incubation of aptamer with target protein in solution, enabling separation and washing of target-bound aptamers. Selection was carried out in a total volume of 100 µl in Dulbecco's PBS (DPBS) with increasing concentration of the non-specific competitor tRNA and washing volume as well as decreasing amounts of target protein to enhance stringency over the course of selection. For round 1, 1×10¹⁴ molecules of the starting pool were used (with a final concentration of 1.66 µM) and in subsequent rounds, the output pool from the previous round were adjusted to 1 µM. The filters were pre-treated with KOH to reduce non-specific binding of the DNA pools to the filter.

For removal of filter-binding aptamers in a negative pre-selection (skipped in round 1), 50 µl pool/DPBS solution were added to pre-treated filters and centrifuged at 2000 rpm for 1 min. The flow-through was collected for use in subsequent positive/negative selection steps.

A counter selection was applied if desired to remove aptamers against components not to be targeted (e.g. His-tags or Fc-fusion portions of applied recombinant target proteins; skipped in round 1) by adding protein and DPBS to the flow-through of negative selection to a final concentration of 1 µM protein in 90 µl total volume. After incubation for 1 h at 37° C., the pool/DPBS solution was added to pre-treated filters, centrifuged at 2000 rpm for 1 min and the flow-through was collected for use in a positive selection step.

Positive selection was carried out in case of a previous counter selection by adding target protein and competitor amount to 90 µl pool/DPBS flow-through to yield 1 µM protein in 100 µl total volume. Positive selection mixtures were incubated 1 h at 37° C., then added to pre-treated Centrex columns and centrifuged at 2000 rpm for 1 min discarding the flow-through. Filters thereby caught desired protein: pool complexes. These were washed two times with pre-warmed 1000 µl DPBS (500 µl in round 1) and centrifugation discarding flow-through as before, and eluted with two times 200 µl 90° C. pre-heated elution buffer by incubation for 1 min and centrifugation as above combining both flow-through elution fractions (400 µl total). During this step, heat and urea denatured target proteins lost their correct folding releasing conformational epitope-binding aptamers that were collected in the flow-through. These aptamers were purified for subsequent PCR via isopropanol precipitation and resuspended in 10 µl dH2O.

Amplification of aptamer pools was achieved in a two-step PCR setup. Initial small scale PCRs (ssPCR) were carried out to adjust DNA concentrations to a standard concentration of 10 ng/µl, at the same time investigating indirectly the amount of selected aptamers by PCR cycle monitoring. The more aptamers were enriched, the less PCR cycles were needed to yield the desired concentration. In the next step, large scale PCRs (lsPCR) followed to yield sufficient aptamer material for subsequent selection rounds. The lsPCR solution was Ethanol-precipitated, and pellets were dried and resuspended in 30 µl TE buffer pH 8.0 and transferred to 1.5 ml tubes.

Single stranded aptamers had to be obtained via strand separation of the double stranded PCR products. The use of 3' ribo-modified reverse primers enabled alkaline induced strand breaks of the anti-sense strand leading to one larger sense strand aptamer and two smaller anti-sense fragments that were separated by polyacrylamide gel electrophoresis Passive gel elution, DNA precipitation, and resuspension in 40 µl DPBS were completed by concentration determination to yield an enriched aptamer pool ready for the next SELEX round.

We selected CD16α aptamers that bind both CD16α (V158) and CD16α(F158) on NK cells, but not CD16β, with high specificity (no binding to other cells or proteins) and high affinity (Kd of two digit nanomolar range or lower).

For the CD16α aptamers some important specifications are given in following table 1:

TABLE 1

Specifications of CD16 DNA SELEX.
Target protein was CD16<-6His ("6His" disclosed as SEQ ID NO: 88) while CD16β-10His ("10His" disclosed as SEQ ID NO: 89) was applied for counter selection, tRNA served as unspecific competitor. PCR cycles needed to re-amplify a certain amount of aptamers were monitored and are highlighted. MTP, microtiterplate.

| Round | DNA conc. (μM) | Protein conc. (μM) | Neg. sel. | Counter sel. (μM) | tRNA (mg/ml) | No. of PCR cycles | DNA conc. (μM) | Protein conc. (μM) | Neg. sel. | Counter sel. (μM) | tRNA (mg/ml) | No. of PCR cycles |
|---|---|---|---|---|---|---|---|---|---|---|---|---|
| | | | DNA filter SELEX I | | | | | | DNA filter SELEX II | | | |
| 1 | 1.66 | 1 | none | 0 | 0 | 10 | 1.66 | 1 | none | 0 | 0 | 10 |
| 2 | 0.62 | 1 | filter | 0 | 0 | 15 | 0.83 | 0.96 | filter | 1 | 0 | 18 |
| 3 | 1 | 1 | filter | 0 | 0 | 20 | 1 | 1 | filter | 1 | 0 | 20 |
| 4 | 1 | 1 | filter | 0 | 0.1 | 17 | 0.75 | 1 | filter | 1 | 0 | 28 |
| 5 | 1 | 0.8 | filter | 0 | 0.1 | 20 | 1 | 1 | filter | 1 | 0.1 | 20 |
| 6 | 1 | 0.8 | filter | 0 | 0.1 | 10 | 1 | 0.8 | filter | 0.8 | 0.1 | 9 |
| 7 | 0.62 | 0.6 | filter | 0 | 0.1 | 10 | 0.69 | 0.6 | filter | 0.6 | 0.1 | 11 |
| 8 | 0.69 | 0.6 | filter | 0 | 0.1 | 7 | 0.96 | 0.6 | filter | 0.6 | 0.1 | 8 |
| 9 | 0.55 | 0.6 | filter | 0 | 1 | 10 | 0.56 | 0.6 | filter | 0.6 | 1 | 10 |
| | | | DNA MTP SELEX 01.09 | | | | | | DNA MTP SELEX 02.09 | | | |
| 10 | 0.7 | 0.2 | none | 1 | 0 | 14 | 0.7 | 0.2 | none | 1 | 0 | 14 |
| 11 | 0.5 | 0.2 | none | 1 | 0 | 21 | 0.6 | 0.2 | none | 1 | 0 | 18 |
| 12 | 1 | 0.2 | filter | 0 | 1 | 11 | 1 | 0.6 | filter | 0 | 1 | 11 |

We selected c-Met aptamers that bind to c-Met on c-Met positive cells with high specificity and affinity (as above). If other Tumour Specific Antigens (TSAs) are applicable, e.g. EGFR, aptamers can also be selected and applied for the construction of bispecific aptamers.
Aptamers may consist of DNA, dRmY, rGmH, rRfY, dCmD, mRfY, MNA or rRnY compositions, with R = purine; Y = pyrimidine; H = A, C, U; D = A, G, U; d = 2' deoxy; r = 2' hydroxy; m = 2' methoxy; f = 2' fluoro; n = 2' amine.

Example 2

Data Obtained - CD16α Aptamers

DNA and rRfY aptamers were selected against CD16α via filter and cell SELEX (DNA filter SELEX: CLN0015-31, cell SELEX: CLN0118-128, rRfY filter SELEX: CLN0047-63).
The sequences of all aptamers binding specifically to CD16 were:
A) DNA Aptamers

```
CLN0015;
                                              SEQ ID NO: 1
GGAGGGAAAAGTTATCAGGCGGCAGAAGAAATATCGAAACCCAGAATGGTCGGCCAGGCGGATT

AGTTTTGGAGTACTCGCTCC

CLN0016;
                                              SEQ ID NO: 2
GGAGGGAAAAGTTATCAGGCCAAGCACAAGAACTTTCAAAACGCAGAATGCTGGGCTTGGGATT

AGTTTTGGAGTACTCGCTCC

CLN0017;
                                              SEQ ID NO: 3
GGAGGGAAAAGTTATCAGGCCAGACGAGAATTTGGAAAACGCGGAACGCCGTCTGGTGTGGATT

AGTTTTGGAGTACTCGCTCC

CLN0018;
                                              SEQ ID NO: 4
GGAGGGAAAAGTTATCAGGCATCACGTGGTGGGCAAATAACCGGTTGGGGTGGGTCGAGGGAT

TAGTTTTGGAGTACTCGCTCC

CLN0019;
                                              SEQ ID NO: 5
GGAGGGAAAAGTTATCAGGCAACGGGAAGAAATGTCGAAACCCTTGAAAGGTCACGGACTGATT

AGTTTTGGAGTACTCGCTCC
```

-continued

CLN0020;
SEQ ID NO: 6
GGAGGGAAAAGTTATCAGGCCACTGCGGGGTCTATACGTGAGGAAGAAGTGGGCAGGTCGAT

TAGTTTTGGAGTACTCGCTCC

CLN0021;
SEQ ID NO: 7
GGAGGGAAAAGTTATCAGGCGCAAGTATGAGCGCAGGAGTTAGGTCCCGTGGCGATGGGTGATT

AGTTTTGGAGTACTCGCTCC

CLN0022;
SEQ ID NO: 8
GGAGGGAAAAGTTATCAGGCGTAGGTGGGGGACTGGGGACGGGTATGGGCACACGGTATGATT

AGTTTTGGAGTACTCGCTCC

CLN0023;
SEQ ID NO: 9
GGAGGGAAAAGTTATCAGGCGACGTTAAGCTAGCAGGTGTTAGGTCCCGTGGTGATGAATGATT

AGTTTTGGAGTACTCGCTCC

CLN0024;
SEQ ID NO: 10
GGAGGGAAAAGTTATCAGGCGGGAGGAGAATTAATAAAAACCCGGGACGGCCGACGGGATGATT

AGTTTTGGAGTACTCGCTCC

CLN0025;
SEQ ID NO: 11
GGAGGGAAAAGTTATCAGGCCAGAACAAAGCGGGAGAATTATGAAAACGCGGAACGCCACGATT

AGTTTTGGAGTACTCGCTCC

CLN0026;
SEQ ID NO: 12
GGAGGGAAAAGTTATCAGGCGCTAAGAGAAATATCGAAACCCTGGATAGGCTGAGTGACTGATTA

GTTTTGGAGTACTCGCTCC

CLN0027;
SEQ ID NO: 13
GGAGGGAAAAGTTATCAGGCAGGTGTAGGCCCTGTGGTGATGAATCGCGTGTCGAGGGGTGATT

AGTTTTGGAGTACTCGCTCC

CLN0028;
SEQ ID NO: 14
GGAGGGAAAAGTTATCAGGCCGCAGCGGAGAAATTTCGAAACCCAGGATGGCCGCGAGGTGATT

AGTTTTGGAGTACTCGCTCC

CLN0029;
SEQ ID NO: 15
GGAGGGAAAAGTTATCAGGCGACGGGACGAAAAACGGTTGGATGAGGTTGGTTGGGTGTGGATT

AGTTTTGGAGTACTCGCTCC

CLN0030;
SEQ ID NO: 16
GGAGGGAAAAGTTATCAGGCTAAACCCCAAAACAGTGCAACTAGGTGTAGGTCCCGTGGTGATT

AGTTTTGGAGTACTCGCTCC

CLN0031;
SEQ ID NO: 17
GGAGGGAAAAGTTATCAGGCGGCCAGAGAAATGTCGAAACCCGGTAACGGATGGTAAGCTGATT

AGTTTTGGAGTACTCGCTCC

CLN0032;
SEQ ID NO: 18
GGAGGGAAAAGTTATCAGGCCAGCCACTGGAGAAAGTAAGAAACGCAGAATGCCCAGTGGGATT

AGTTTTGGAGTACTCGCTCC

-continued

CLN0118;
SEQ ID NO: 19
GGAGGGAAAAGTTATCAGGCACGGACTCGCAAAAGGTGGAACAGGAGTGGGCCCCGCGGCGAT

TAGTTTTGGAGTACTCGCTCC

CLN0119;
SEQ ID NO: 20
GGAGGGAAAAGTTATCAGGCTGCGGCGAGAAATGTCGAAACGGTGAAACCCGCCATGCGTGATT

AGTTTTGGAGTACTCGCTCC

CLN0120;
SEQ ID NO: 21
GGAGGGAAAAGTTATCAGGCCACCCGTCAGGGGTTCGTTGTGAGGAGAGAGGGTTGGGCCGAT

TAGTTTTGGAGTACTCGCTCC

CLN0121;
SEQ ID NO: 22
GGAGGGAAAAGTTATCAGGCCGAGTGAAAGAGGCAGGTGTAGGTCCCGTGGAGGTCAGGTGAT

TAGTTTTGGAGTACTCGCTCC

CLN0122;
SEQ ID NO: 23
GGAGGGAAAAGTTATCAGGCAGGCGCGAGAAATATCGAAACACCGGACGGTCGCGACGCTGATT

AGTTTTGGAGTACTCGCTCC

CLN0123;
SEQ ID NO: 24
GGAGGGAAAAGTTATCAGGCAGAGGGGAGGGTCGGGTATCGGCGTGTTCGGGGATCTGCGAT

TAGTTTTGGAGTACTCGCTCC

CLN0124;
SEQ ID NO: 25
GGAGGGAAAAGTTATCAGGCCCGGGAGAATTAGATTAAAACGCGGAACGCCCCGTGCCCGGATT

AGTTTTGGAGTACTCGCTCC

CLN0125;
SEQ ID NO: 26
GGAGGGAAAAGTTATCAGGCAGTGTAGGGAGCGGAGTAGGCAGGCGTAGGTCCTGTGGTGATT

AGTTTTGGAGTACTCGCTCC

CLN0126;
SEQ ID NO: 27
GGAGGGAAAAGTTATCAGGCGGCGTTGTCGGGCGCAGGTGTAGGCCTCGTGGTGGTGGGTGAT

TAGTTTTGGAGTACTCGCTCC

CLN0127;
SEQ ID NO: 28
GGAGGGAAAAGTTATCAGGCGGGGGACAAGGGTCGGGTATGGGCGCCTCGAGAACTGGGTGAT

TAGTTTTGGAGTACTCGCTCC

CLN0128;
SEQ ID NO: 29
GGAGGGAAAAGTTATCAGGCATAGGCAACGGGGATGATAACCAGTTGGGGTGGGACGAGGGAT

TAGTTTTGGAGTACTCGCTCC

B) rRfY CD16 Specific Aptamers

CLN0047;
SEQ ID NO: 30
GGAGGGAAAAGTTATCAGGCTGCGGAAGGTAGGTTATACGAGCGCGCAGGACTGGTAATAGATT

AGTTTTGGAGTACTCGCTCC

CLN0048;
SEQ ID NO: 31
GGAGGGAAAAGTTATCAGGCAGTGAGAGGTTAAAGGAAGGGTGCGTTGTCAAAGGCTGGTGATT

AGTTTTGGAGTACTCGCTCC

CLN0049;
SEQ ID NO: 32
GGAGGGAAAAGTTATCAGGCGTAAGCGAAGGGTCAAAAAGGCCGAGCGGTTTAGGCATCAGATT

AGTTTTGGAGTACTCGCTCC

CLN0050;
SEQ ID NO: 33
GGAGGGAAAAGTTATCAGGCTAAACCCCAAAACAGTGCAACTAGGTGTAGGTCCCGTGGTGATT

AGTTTTGGAGTACTCGCTCC

CLN0051;
SEQ ID NO: 34
GGAGGGAAAAGTTATCAGGCCCGGCTTCGAAGGGTGAATACTGAGCGGAAGTGAGAGGAAGATT

AGTTTTGGAGTACTCGCTCC

CLN0052;
SEQ ID NO: 35
GGAGGGAAAAGTTATCAGGCGCAAGGAGGTAAAAGGAAGGGTGGTTGCTTGGCGCTAACGGATT

AGTTTTGGAGTACTCGCTCC

CLN0053;
SEQ ID NO: 36
GGAGGGAAAAGTTATCAGGCGTAATGGAAGGGCGTTATGAACGCTGAGCGCATTAGGGGTGATT

AGTTTTGGAGTACTCGCTCC

CLN0054;
SEQ ID NO: 37
GGAGGGAAAAGTTATCAGGCCTAGTGTTATGACCCTAGAAATAGATGAGTTGAGAGGTCGGATTA

GTTTTGGAGTACTCGCTCC

CLN0055:
SEQ ID NO: 38
GGAGGGAAAAGTTATCAGGCGCATGTGAAGGGACCAATCCGAGCGACATGGTGCGGGATAGATT

AGTTTTGGAGTACTCGCTCC

CLN0056:
SEQ ID NO: 39
GGAGGGAAAAGTTATCAGGCTATGGAAGGGATAGGGTATCCGAGCGCAGAGGCTGAGGATTAGT

TTTGGAGTACTCGCTCC

CLN0057;
SEQ ID NO: 40
GGAGGGAAAAGTTATCAGGCATAGAGGTGAGAGGAAGGGTGTGTTGTATGTTGATAACGAGATT

AGTTTTGGAGTACTCGCTCC

CLN0058;
SEQ ID NO: 41
GGAGGGAAAAGTTATCAGGCTCACGAAGTCAGCAATAATTTGCTGTAGGCGGTGGGACTGATT

AGTTTTGGAGTACTCGCTCC

CLN0059;
SEQ ID NO: 42
GGAGGGAAAAGTTATCAGGCACGTAGTGGGAGGACGCGGAAAGTCGAGCGCATTAGGTGGGAT

TAGTTTTGGAGTACTCGCTCC

CLN0060;
SEQ ID NO: 43
GGAGGGAAAAGTTATCAGGCGCGGTGGAAGGCTGAACATTGGCGAGCGCATCGGAGATCTGATT

AGTTTTGGAGTACTCGCTCC

CLN0061;
SEQ ID NO: 44
GGAGGGAAAAGTTATCAGGCCAGAGAAACATAAACCATAAACGCAGAAGCTGGCTGTGAGGATT

AGTTTTGGAGTACTCGCTCC

```
CLN0062;
                                                      SEQ ID NO: 45
GGAGGGAAAAGTTATCAGGCGTTCTTGTAGTGCATCCAATTGCAGAGCGAAGGAGGTGTTGATTA

GTTTTGGAGTACTCGCTCC

CLN0063;
                                                      SEQ ID NO: 46
GGAGGGAAAAGTTATCAGGCACGTAGTTGAAGGACTTTTGGGTTGAGCGGACTAGGTGTAGATT

AGTTTTGGAGTACTCGCTCC
```

C) mRfY CD16 Spezifische Aptamere

```
CLN0072;
                                                      SEQ ID NO: 47
GGAGGGAAAAGTTATCAGGCAATGACATATTTCTTATATCGGGTTTGGAGTGCCTTGCCTAGATTA

GTTTTGGAGTACTCGCTCC

CLN0076:
                                                      SEQ ID NO: 48
GGAGGGAAAAGTTATCAGGCAATGACATTTTCTTATATCGGGTTTGGAGTGCCCTGCCTAGATTA

GTTTTGGAGTACTCGCTCC

CLN0077;
                                                      SEQ ID NO: 49
GGAGGGAAAAGTTATCAGGCATGTATTGCGGATGATTTTGTATTTAATGTGTATGCCTCGGATTAG

TTTTGGAGTACTCGCTCC
```

Only DNA CD16α aptamers were characterised further, resulting in only 3 candidates:

CLN0020 (SEQ ID NO:6):

Biochemical binding and affinity: 45 ±28 nM (n =10) against CD16a-6His ("6His" disclosed as SEQ ID NO: 88), both V158 and F158 allotype binding, no CD16β binding at all, no His-tag binding, data by dot blot. Cellular binding confirmed by FACS on 1) recombinant CD16a(V158)-positive Jurkat cell line, 2) recombinant CD16α(F158)-positive Jurkat cell line, 3) freshly isolated CD16α-positive PBMCs (including NK cells), 4) freshly isolated NK cells. No unspecific binding seen on CD16α negative cell lines Jurkat E6.1, CD16α-negative PBMCs, GTL-16. Epitope mapping via competition dot blot against cetuximab (Bou-Assaly and Mukherji (2010) AJNR Am J Neuroradiol 31(4):626-7) and CD16α-specific mAb 3G8 showed that CLN0020 binds in or near the Fc binding domain (analogue to antibodies, only with ~10× higher affinity). Structure prediction driven minimisation lead to a shortened version (41 mer instead of 84 mer, named "MS1", and 34 mer named "MS3", see below) that exhibits similar properties to the FL aptamer. Serum stability in FBS showed a half life of ~10 h.

CLN0123 (SEQ ID NO:24):

Biochemical binding and affinity: 231 nM against CD16α-6His ("6His" disclosed as SEQ ID NO: 88), V158 allotype binding only, no CD16β binding at all, no His-tag binding, data by dot blot. Competition dot blot against CLN0020 revealed that CLN0123 binds to a different epitope, hence not in the Fc binding site, thus does not compete with serum IgG. Cellular binding confirmed by FACS on 1) recombinant CD16a(V158)-positive Jurkat cell line, 2) recombinant CD16α(F158)-positive Jurkat cell line, 3) freshly isolated PBMCs (including NK cells), 4) freshly isolated NK cells. No unspecific binding seen on CD16αnegative cell lines Jurkat E6.1, CD16-negative PBMCs.

CLN0018 (SEQ ID NO:4):

Biochemical binding and affinity: 38 ±26 nM (n=4) against CD16α-6His ("6His" disclosed as SEQ ID NO: 88), V158 allotype binding only, no CD16β binding at all, no His-tag binding, data by dot blot. Cellular binding analysis via FACS showed broad unspecific binding.

Example 3

DNA c-Met Aptamers c-Met DNA aptamers were selected by filter SELEX on recombinant Fc-c-Met.

The sequences of all aptamers binding specifically to c-met were:

```
CLN0001;
                                                      SEQ ID NO: 50
GGAGGGAAAAGTTATCAGGCCGGGTGGGAGTAACAGGCTGTTGGTAGGGGTGGACCTGGAT

TAGTTTTGGAGTACTCGCTCC

CLN0002;
                                                      SEQ ID NO: 51
GGAGGGAAAAGTTATCAGGCAAAGGAGAAGGTCCAAAACGGCCTGGGTGGTGGGTATGTGGATT

AGTTTTGGAGTACTCGCTCC
```

-continued

CLN0003;
SEQ ID NO: 52
GGAGGGAAAAGTTATCAGGCTGGATGGTAGCTCGGTCGGGGTGGGTGGGTTGGCAAGTCTGAT

TAGTTTTGGAGTACTCGCTCC

CLN0004;
SEQ ID NO: 53
GGAGGGAAAAGTTATCAGGCGAGTGCGTAATGGTACGATTTGGGAAGTGGCTTGGGGTGGATT

AGTTTTGGAGTACTCGCTCC

CLN0005;
SEQ ID NO: 54
GGAGGGAAAAGTTATCAGGCAAAGGAGAAGGCTCAAAACGGCCTGGGTGGTGGGTATGTGGATT

AGTTTTGGAGTACTCGCTCC

CLN0006;
SEQ ID NO: 55
GGAGGGAAAAGTTATCAGGCGGATACAGCAGAATAAGGGAAGGGGCAGATCGGGTGGGGATT

AGTTTTGGAGTACTCGCTCC

CLN0007;
SEQ ID NO: 56
GGAGGGAAAAGTTATCAGGCAGCAAACAGCAGGTAGAGGGAAGTGGCAGATCGGGTGGGGAT

TAGTTTTGGAGTACTCGCTCC

CLN0008;
SEQ ID NO: 57
GGAGGGAAAAGTTATCAGGCGAGCGGGGACGAACACATATGGGGAAGTGGCTTGGGGTGGGAT

TAGTTTTGGAGTACTCGCTCC

CLN0009;
SEQ ID NO: 58
GGAGGGAAAAGTTATCAGGCGAGTGCGTAATGGTACGATTTGGGAAGTGGTTTGGGGTGGGATT

AGTTTTGGAGTACTCGCTCC

CLN0010;
SEQ ID NO: 59
GGAGGGAAAAGTTATCAGGCCGACAGTGGGTAGCGGTTAAGGGGAAGTGGCTTGGGGTGGGAT

TAGTTTTGGAGTACTCGCTCC

CLN0011;
SEQ ID NO: 60
GGAGGGAAAAGTTATCAGGCCGGGGTGGGATAAAAGCATGGTTGGTAGGGGTTGGGGCATGAT

TAGTTTTGGAGTACTCGCTCC

CLN0012;
SEQ ID NO: 61
GGAGGGAAAAGTTATCAGGCAAGGCGTGTGTATCCCTGTGGTAGGGGTTGGTCGGGGTGGGAT

TAGTTTTGGAGTACTCGCTCC

CLN0013;
SEQ ID NO: 62
GGAGGGAAAAGTTATCAGGCCAGGGTCGGGATTGGGCGGGGTCTGGAAGATCATGTGCCAGAT

TAGTTTTGGAGTACTCGCTCC

CLN0014;
SEQ ID NO: 63
GGAGGGAAAAGTTATCAGGCCGGGGGGGAAGACGAGTGTAAGTTGGTAGGGTGGGGTAGGAT

TAGTTTTGGAGTACTCGCTCC

Only 2 aptamers meet the criteria of low nanomolar binding and were characterised further (CLN0008 excluded due to high sequence similarity with CLN0004):

CLN0003 (SEQ ID NO53):

Biochemical binding and affinity: 91±40 pM (n=3) against Fc-His-c-Met no Fc-binding, no His-tag binding, data by dot blot. Cellular binding confirmed by FACS on c-Met positive cell lines GTL-16, MNK-45, EBC-1; no unspecific binding seen on Jurkat cells. Minimisation was applied but not successful (see below).

CLN0004 (SEQ ID NO54):

Biochemical binding and affinity: 11±6 nM (n=6) against Fc-His-c-Met no Fc-binding, no His-tag binding, data by dot blot. Cellular binding confirmed by FACS on c-Met positive cell lines GTL-16, MNK-45, EBC-1; no unspecific binding seen on Jurkat cells. Minimisation lead to a shortened version (41mer instead of 84mer, named "MS2", see below) that exhibits similar properties to the FL aptamer. Serum stability in FBS showed a half life of ~10 h.

Example 4

Bispecific Aptamers

Bispecific Aptamers
Linkage of a TRA entity with a ESA entity via a linker:
The following different types of linkers have been employed:
PEG(3), PEG(6), PEG(24)
nucleotides: 15dA
nucleotides "linker sequence of flanking sequence" 7-24 nt long)

Linkage has been accomplished in a manner that constitutes a distance between the both aptamer entities that correlates to the distance of CDRs to Fc binding domain in antibodies (~7.5 nm).
Establishment of coupling the two aptamers by different strategies
1. Direct full synthesis incorporating nucleotide or carbon/PEG linker of several sequences and lengths (see below).
2. Coupling of
   5' an amine-functionalised aptamer with C7 carbon spacer to NHS-activated PEG(24) and
   3' a thiol-functionalised aptamer with C3 carbon spacer to maleimide bound to the other end of PEG(24)
   Resulting in a final construct: aptamer1-C7-NH—CO—PEG(24)-maleimide-S—C3-aptamer2
The following bispecific aptamers have been constructed:
CD16 c-Met Bispecific DNA Aptamers

```
bsA1;
                                                       SEQ ID NO: 64
CCACTGCGGGGGTCTATACGTGAGGAAGAAGTGGGCAGGTCGAGTGCGTAATGGTACGATTTGG

GAAGTGGCTTGGGGTGGG bsA2;
                                                       SEQ ID NO: 65
GAGTGCGTAATGGTACGATTTGGGAAGTGGCTTGGGGTGGGCCACTGCGGGGGTCTATACGTG

AGGAAGAAGTGGGCAGGTC bsA3;
                                                       SEQ ID NO: 66
CCACTGCGGGGGTCTATACGTGAGGAAGAAGTGGGCAGGTCAAAAAAAAAAAAAAAGAGTGCGT

AATGGTACGATTTGGGAAGTGGCTTGGGGTGGG bsA31;
                                                       SEQ ID NO: 67
CCACTGCGGGGGTCTATACGTGAGGAAGAAGTGGGCAGGTCAAAAAAAAAAAAAAAGAGTGCGT

AATGGTACGATTTGGGAAGTGGCTTGGGGTGGGATTAGTTTTGGAGTACTCGCTCC bsA32;
                                                       SEQ ID NO: 68
CCACTGCGGGGGTCTATACGTGAGGAAGAAGTGGAAAAAAAAAAAAAAAGAGTGCGTAATGGTA

CGATTTGGGAAGTGGCTTGGGGTGGGATTAGTTTTGGAGTACTCGCTCC bsA4;
                                                       SEQ ID NO: 69
GAGTGCGTAATGGTACGATTTGGGAAGTGGCTTGGGGTGGGAAAAAAAAAAAAAAACCACTGCG

GGGGTCTATACGTGAGGAAGAAGTGGGCAGGTC bsA5;
                                                  SEQ ID NOS 70 and 90
CCACTGCGGGGGTCTATACGTGAGGAAGAAGTGGGCAGGTC/iSp9/GAGTGCGTAATGGTACGAT

TTGGGAAGTGGCTTGGGGTGGG bsA6;
                                                  SEQ ID NOS 71 and 91
GAGTGCGTAATGGTACGATTTGGGAAGTGGCTTGGGGTGGG/iSp9/CCACTGCGGGGGTCTATAC

GTGAGGAAGAAGTGGGCAGGTC bsA7;
                                                  SEQ ID NOS 72 and 92
CCACTGCGGGGGTCTATACGTGAGGAAGAAGTGGGCAGGTC/iSp18/GAGTGCGTAATGGTACGA

TTTGGGAAGTGGCTTGGGGTGGG
``` bsA8;
SEQ ID NOS 73 and 93
GAGTGCGTAATGGTACGATTTGGGAAGTGGCTTGGGGTGGG/iSp18/CCACTGCGGGGGTCTATA
CGTGAGGAAGAAGTGGGCAGGTC bsA9;
SEQ ID NO: 74
GGAGGGAAAAGTTATCAGGCCACTGCGGGGGTCTATACGTGAGGAAGAAGTGGGCAGGTCGAT

TAGTTTTGGAGTACTCGCTCCGGAGGGAAAAGTTATCAGGCTGGATGGTAGCTCGGTCGGGGTG

GGTGGGTTGGCAAGTCTGATTAGTTTTGGAGTACTCGCTCC bsA10;
SEQ ID NO: 75
GGAGGGAAAAGTTATCAGGCTGGATGGTAGCTCGGTCGGGGTGGGTGGGTTGGCAAGTCTGAT

TAGTTTTGGAGTACTCGCTCCGGAGGGAAAAGTTATCAGGCCACTGCGGGGGTCTATACGTGAG

GAAGAAGTGGGCAGGTCGATTAGTTTTGGAGTACTCGCTCC bsA11;
SEQ ID NO: 76
CCACTGCGGGGGTCTATACGTGAGGAAGAAGTGGGCAGGTCGATTAGTTTTGGAGTACTCGCTC

CGGAGGGAAAAGTTATCAGGCTGGATGGTAGCTCGGTCGGGGTGGGTGGGTTGGCAAGTCTGA

TTAGTTTTGGAGTACTCGCTCC bsA12;
SEQ ID NO: 77
CCACTGCGGGGGTCTATACGTGAGGAAGAAGTGGGCAGGTCGATTAGTTTTGGAGTACTCGCTC

CGGAGGGAAAAGTTATCAGGCGAGTGCGTAATGGTACGATTTGGGAAGTGGCTTGGGGTGGGAT

TAGTTTTGGAGTACTC bsA13;
SEQ ID NO: 78
GAGTGCGTAATGGTACGATTTGGGAAGTGGCTTGGGGTGGGATTAGTTTTGGAGTACTCGCTCC

GGAGGGAAAAGTTATCAGGCCACTGCGGGGGTCTATACGTGAGGAAGAAGTGG bsA14;
SEQ ID NO: 79
GGAGGGAAAAGTTATCAGGCTGGATGGTAGCTCGGTCGGGGTGGGTGGGTTGGCAAGTCTGAT

TAGTTTTGGAGTACTCGCTCC-C7-NH2
and

GTTATCAGGCCACTGCGGGGGTCTATACGTGAGGAAGAAGTGGGCAGGTC-C3-SH (SEQ ID NO: 94)
with functional residues NH2 and SH linked by PEG(24) to yield aptamer1-
C7-NH—CO-PEG(24)-maleimide-S—C3-aptamer2 bsA15;
SEQ ID NO: 80
GGAGGGAAAAGTTATCAGGCAGAGGGGAGGGTCGGGTATCGGCGTGTTCGGGGGATCTGCGAT

TAGTTTTGGAGTACTCGCTCCGGAGGGAAAAGTTATCAGGCTGGATGGTAGCTCGGTCGGGGTG

GGTGGGTTGGCAAGTCTGATTAGTTTTGGAGTACTCGCTCC bsA16;
SEQ ID NO: 81
GAGTGCGTAATGGTACGATTTGGGAAGTGGCTTGGGGTGGGATTAGTTTTGGAGTACTCGCTCC

GGAGGGAAAAGTTATCAGGCAGAGGGGAGGGTCGGGTATCGGCGTGTTCGGGGATCTGCGAT

TAGTTTTGGAGTACTCGCTCC bsA17;
SEQ ID NO: 82
CCACTGCGGGGGTCTATACGTGAGGAAGAAGTGGGCAGGTCGGAGGGAAAAGTTATCAGGCTG

GATGGTAGCTCGGTCGGGGTGGGTGGGTTGGCAAGTCTGATTAGTTTTGGAGTACTCGCTCC

-continued bsA18;
SEQ ID NO: 83
CCACTGCGGGGGTCTATACGTGAGGAAGAAGTGGGCAGGTCATCAGGCGAGTGCGTAATGGTA
CGATTTGGGAAGTGGCTTGGGGTGGGATTAGTTTTGGAGTACTC bsA19;
SEQ ID NO: 84
CCACTGCGGGGGTCTATACGTGAGGAAGAAGTGGGCAGGTCAAAAAAAAAAAAAAAGGAGGGAA
AAGTTATCAGGCTGGATGGTAGCTCGGTCGGGGTGGGTGGGTTGGCAAGTCT bsA20;
SEQ ID NO: 85
CCACTGCGGGGGTCTATACGTGAGGAAGAAGTGGGCAGGTCGGAGGGAAAAGTTATCAGGCTG
GATGGTAGCTCGGTCGGGGTGGGTGGGTTGGCAAGTCT bsA21;
SEQ ID NO: 86
CCACTGCGGGGGTCTATACGTGAGGAAGAAGTGGGCAGGTCAAAAAAAAAAAAAAAGGAGGGAA
AAGTTATCAGGCTGGATGGTAGCTCGGTCGGGGTGGGTGGGTTGGCAAGTCTGATTAGTTTTGG
AGTACTCGCTCC bsA22;
SEQ ID NO: 87
CCACTGCGGGGGTCTATACGTGAGGAAGAAGTGGAAAAAAAAAAAAAAAGGAGGGAAAAGTTAT
CAGGCTGGATGGTAGCTCGGTCGGGGTGGGTGGGTTGGCAAGTCTGATTAGTTTTGGAGTACTC
GCTCC The following table 2 shows details of the bispecific aptamers of the invention. Table discloses SEQ ID NOS 95, 95-96, 95, 97-98, 97, 99-102, 95, and 95-96, respectively, in order of appearance.

| Construct | 5' aptamer | Linker sequence | 3' aptamer | Putative linker length (Å) | $M_w$ |
|---|---|---|---|---|---|
| bsA1 | -19CLN0020-24 | GCAGGTC | -20CLN0004-23 | 49 | 25800 |
| bsA2 | -20CLN0004-23 | none | -19CLN0020-24 | 0 | 25800 |
| bsA3 | -19CLN0020-24 | GCAGGTCAAAAAAAAAAAAAAA | -20CLN0004-23 | 154 | 30500 |
| bsA31 | -19CLN0020-24 | GCAGGTCAAAAAAAAAAAAAAA | -20CLN0004 | 154 | 37600 |
| bsA32 | -19CLN0020-31 | AAAAAAAAAAAAAAA | -20CLN0004 | 105 | 35400 |
| bsA4 | -20CLN0004-23 | GCAGGTCAAAAAAAAAAAAAAA | -19CLN0020-24 | 154 | 30500 |
| bsA5 | -19CLN0020-24 | GCAGGTC + PEG$_{(3)}$ = C$_9$ | -20CLN0004-23 | 69 | 26000 |
| bsA6 | -20CLN0004-23 | PEG$_{(3)}$ = C$_9$ | -19CLN0020-24 | 20 | 26000 |
| bsA7 | -19CLN0020-24 | GCAGGTC + PEG$_{(6)}$ = C$_{18}$ | -20CLN0004-23 | 82 | 26100 |
| bsA8 | -20CLN0004-23 | PEG$_{(6)}$ = C$_{18}$ | -19CLN0020-24 | 33 | 26100 |
| bsA9 | CLN0020 | GCAGGTCGATTAGTTTTGGAGTACTCGCTCC | CLN0003 | 217 | 52700 |
| bsA10 | CLN0003 | GGAGGGAAAAGTTATCAGG | CLN0020 | 133 | 52700 |
| bsA11 | -19CLN0020 | GCAGGTCGATTAGTTTTGGAGTACTCGCTCC | CLN0003 | 217 | 46600 |
| bsA12 | -19CLN0020 | GCAGGTCGATTAGTTTTGGAGTACTCGCTCCGGAGGGAAAAGTTATCAGGC | CLN0004-5 | 357 | 45100 |
| bsA13 | -20CLN0004 | GCTCCGGAGGGAAAAGTTATCAGG | CLN0020-31 | 168 | 36700 |
| bsA14 | -10CLN0020-24 | GCAGGTC + PEG$_{(24)}$ = C$_{72}$ | CLN0003 | 144 | 42800 |
| bsA15 | CLN0123 | GATTAGTTTTGGAGTACTC | CLN0003 | 140 | 52700 |
| bsA16 | -20CLN0004 | ATTAGTTTTGGAGTACTCGCTCCGGAGGGAAAAGTTATCAGGC | CLN0123 | 308 | 46400 |

| Construct | 5' aptamer | Linker sequence | 3' aptamer | Putative linker length (Å) | $M_w$ |
|---|---|---|---|---|---|
| bsA17 | -19CLN0020-24 | GCAGGTC | CLN0003 | 49 | 39200 |
| bsA18 | -19CLN0020-31 | ATCAGGC | -13CLN0004-5 | 49 | 33500 |
| bsA19 | -19CLN0020-24 | GCAGGTCAAAAAAAAAAAAAAA | CLN0003-24 | 154 | 36400 |
| bsA20 | -19CLN0020-24 | GCAGGTC | CLN0003-24 | 49 | 31700 |
| bsA21 | -19CLN0020-24 | GCAGGTCAAAAAAAAAAAAAAA | CLN0003 | 154 | 43800 |
| bsA22 | -19CLN0020-31 | AAAAAAAAAAAAAA | CLN0003 | 105 | 41700 |

Example 5

Details on Bispecific Aptamers

For bispecific aptamers the following experiments were carried out:
  dot blots to ascertain unchanged binding properties of the respective aptamer entity (Kds see below)
The respective data are summarized in FIG. 2.
Electrophoretic Motility Shift Assay (EMSA) to prove the simultaneous binding of both proteins (band shift of aptamer on TBE-gel when bound to both target proteins) is shown in FIG. 3.

Example 6

Serum Stability of Selected Aptamers

Fetal Bovine Serum Stability for important single Aptamers (CLN0004, CLN0020) and bispecific constructs (bsA3 and bsA17) was determined with serum half lives of 6.4-20.3 h. The results obtained are set forth in FIG. 4.

Example 7

ADCC Assays to Evaluate Tumour Cell Lysis

The following cell lines were used:
  GTL-16 Human gastric adenocarcinoma (Paolo Porporato Novara, Merck KGaA)
  EBC-1 Human lung squamous cell carcinoma (Health Sc. Res. Resources Bank, JCRB0920, 031496)
All ADCC assays were performed using GTL-16 cells (see van der Horst 2009 c-Met antibody ADCC assays), except for bsA17 which was also evaluated using EBC-1 (see FIG. 5, part C). It can be readily taken from FIG. 5 that the bispecific aptamers of the invention mediate a ADCC activity similar to cetuximab FIG. 6 shows the results obtained for bsA22.

The invention claimed is:

1. A bispecific aptamer which specifically binds to a tumor related antigen (TRA) which is c-Met and an effector specific antigen (ESA) which is CD16a.

2. The bispecific aptamer of claim 1, comprising a nucleic acid sequence selected from the group consisting of SEQ ID NO 82 and SEQ ID NO 87.

3. A pharmaceutical composition comprising a bispecific aptamer of claim 1 and a pharmaceutically effective excipient.

4. The pharmaceutical composition of claim 3 effective as a cancer medicament.

5. A method of treating cancer, comprising administering to a patient in need of such treatment an effective amount of a bispecific aptamer of claim 1.

6. A method of treating cancer, comprising administering to a patient in need of such treatment an effective amount of a pharmaceutical composition of claim 3.

7. "The bispecific aptamer of claim 1", wherein said aptamer is effective for the treatment of cancer.

8. The bispecific aptamer of claim 7, comprising a nucleic acid sequence selected from the group consisting of SEQ ID NO 82 and SEQ ID NO 87.

\* \* \* \* \*